(12) United States Patent
Swanson et al.

(10) Patent No.: US 10,040,838 B2
(45) Date of Patent: Aug. 7, 2018

(54) CRHR2 PEPTIDE AGONISTS AND USES THEREOF

(75) Inventors: Ronald V. Swanson, Del Mar, CA (US); Nigel P. Shankley, Solana Beach, CA (US); Veronica Moreno, San Diego, CA (US); Peter Gengo, Carlsbad, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 2103 days.

(21) Appl. No.: 12/612,548

(22) Filed: Nov. 4, 2009

(65) Prior Publication Data

US 2010/0130424 A1 May 27, 2010

Related U.S. Application Data

(60) Provisional application No. 61/111,233, filed on Nov. 4, 2008, provisional application No. 61/178,890, filed on May 15, 2009.

(51) Int. Cl.
*C07K 14/57* (2006.01)
*A61K 38/00* (2006.01)
*C07K 14/575* (2006.01)

(52) U.S. Cl.
CPC ........ *C07K 14/57509* (2013.01); *A61K 38/00* (2013.01)

(58) Field of Classification Search
CPC .......................... C07K 14/57509; A61K 38/00
See application file for complete search history.

(56) References Cited

U.S. PATENT DOCUMENTS

| | | |
|---|---|---|
| 5,272,071 A | 12/1993 | Chappell |
| 5,554,728 A | 9/1996 | Basava et al. |
| 5,766,897 A | 6/1998 | Braxton |
| 6,420,339 B1 | 7/2002 | Gregg et al. |
| 6,552,170 B1 | 4/2003 | Thompson et al. |
| 6,673,580 B2 | 1/2004 | Koren et al. |
| 6,812,210 B2 | 11/2004 | Vale, Jr. et al. |
| 6,828,401 B2 | 12/2004 | Nho et al. |
| 6,869,932 B2 | 3/2005 | Veronese et al. |
| 6,953,838 B2 | 10/2005 | Vale, Jr. et al. |
| 7,230,068 B2 | 6/2007 | Wilson |
| 7,291,341 B2 | 11/2007 | Hsu et al. |
| 2006/0210526 A1 | 9/2006 | Brocchini et al. |
| 2008/0167231 A1 | 7/2008 | Ulich et al. |
| 2008/0261863 A1* | 10/2008 | Whelan et al. .......... 514/4 |

FOREIGN PATENT DOCUMENTS

| | | | |
|---|---|---|---|
| EP | 1 724 283 A2 | 11/2006 | |
| WO | WO 91 06667 A1 | 5/1991 | |
| WO | WO 02 34934 A2 | 5/2002 | |
| WO | WO 02 074326 A2 | 9/2002 | |
| WO | WO 02 094342 A2 | 11/2002 | |
| WO | WO 03/047421 * | 6/2003 | |
| WO | WO 03/062268 * | 7/2003 | C07K 14/00 |
| WO | WO 03 062268 | 7/2003 | |
| WO | WO-2006/082517 | 8/2006 | |
| WO | WO 2006 136586 A2 | 12/2006 | |
| WO | WO 2007 090087 A2 | 8/2007 | |
| WO | WO 2008 047241 A2 | 4/2008 | |
| WO | WO 2009 027844 A2 | 3/2009 | |
| WO | WO 2009/034188 A1 | 3/2009 | |
| WO | WO 2009 040027 A1 | 4/2009 | |
| WO | WO 2010 053990 A2 | 5/2010 | |
| WO | WO 2011/041897 A1 | 4/2011 | |
| WO | WO 2013/012866 A1 | 1/2013 | |

OTHER PUBLICATIONS

Lin et al., 1991, Bivalent ACTH Antagonists: Influence of Peptide and Spacer Components on Potency Enhancement, Biochemical Pharmacology, 41(5): 789-795.*
International Search Report for Corresponding International Application No. PCT/US2009/063276 Mailed on May 7, 2010, 8 Pgs.
Anderson et al "Preparation of a Cell-Free Protein-Synthesizing System From Wheat Germ" Meth Enzymol 1983 vol. 101 pp. 635-644.
Bagshawe et al "Antibody-Directed Enzyme Prodrug Therapy: A Review" Drug Dev Res 1995 vol. 34 pp. 220-230.
Bale et al "The Cardiovascular Physiologic Actions of Urocortin II: Acute Effects in Murine Heart Failure" Proc Natl Acad Sci 2004 vol. 101 pp. 3697-3702.
Bale et al "Mice Deficient for Corticotropin-Releasing Hormone Receptor-2 Display Anxiety-Like Behaviour and Are Hypersensitive to Stress" Nat Genet 2000 vol. 24 pp. 410-414.
Berge et al Pharmaceutical Salts J Pharm Sci 1977 vol. 66 pp. 1-19.
Bertolini et al "A New Rational Hypothesis for the Pharmacophore of the Active Metabolite of Leflunomide, a Potent Immunosuppressive Drug" Med Chem 1997 vol. 40 pp. 2011-2016.
Bodanszky et al Peptide Synthesis 1976 John Wiley & Sons 2nd Ed, TOC only, 6 pages.
Bodor "Novel Approaches to the Design of Safer Drugs: Soft Drugs and Site-Specific Chemical Delivery Systems" Adv Drug Res 1984 vol. 13 pp. 224-331.
Brar et al "Urocortin-ii and Urocortin-III Are Cardioprotective Against Ischemia Reperfusion Injury: An Essential Endogeneous Cardioprotective Role for Corticotropin Releasing Factor Receptor Type -2 in the Murine Heart" Endocrinology 2004 vol. 145(1) pp. 24-35.
Brauns et al "Differential Responsiveness of CRF Receptor Subtypes to N-Terminal Truncation of Peptidic Ligands" Peptides 2002 vol. 23 pp. 881-888.

(Continued)

*Primary Examiner* — Amber D Steele

(74) *Attorney, Agent, or Firm* — Porzio, Bromberg & Newman P.C.

(57) ABSTRACT

The present invention relates to novel peptides that are selective corticotrophin releasing hormone receptor type 2 (CRHR2) agonists and compositions thereof for the treatment, amelioration or inhibition of cardiovascular conditions, including but not limited to heart failure. The novel peptide agonist preferably comprise modifications that include pegylated peptides. Furthermore, the present invention also relates to methods for the treatment and prevention of a disease or disorder related to CRHR2 activity.

21 Claims, 7 Drawing Sheets

(56) References Cited

OTHER PUBLICATIONS

Bundgaard et al Design of Prodrugs 1985 Ed H Bundgaarad Elsevier, 3 pages total.
Cottingham et al "A Method for the Amidation of Recombinant Peptides Expressed as Intein Fusion Proteins in *Escheria coli*" Nature Biotechnology 2001 vol. 19 pp. 974-977.
Cuffe et al "Short-Term Intravenouus Milrinone for Acute Exacerbation of Chronic Heart Failure" JAMA 2002 vol. 287(12) pp. 1541-1547.
Davis et al "Urocortin 2 Infusion in Healthy Humans" J Am Coll Cardiol 2007 vol. 49 pp. 461-471.
Davis et al "Urocortin-2 Infusion in Human Heart Failure" Eur Heart J 2007 vol. 28 pp. 2589-2597.
Fleisher et al "Improved Oral Drug Delivery: Solubility Limitations Overcome by the Use of Prodrugs" Adv Drug Delivery Rev 1996 vol. 19 pp. 115-130.
Freshney Culture of Animal Cells: A Manual of Basic Technique 1994 3rd Ed. Publisher Wiley-LISS, TOC only, 13 pages total.
Grace et al "Common and Divergent Structural Features of a Series of Corticotropin Releasing Facator-Related Peptides" J Am Chem Soc 2007 vol. 129 pp. 16102-16114.
Greenwald et al Drug Delivery Systems 2. Camptothecin 20-O-Poly(Ethylene Glycol) Ester Transport Forms J Med Chem 1996 vol. 39 (10) pp. 1938-1940.
Greenwald et al "Effective Drug Delivery by Pegylated Drug Conjugates" Adv Drug Del Rev 2003 vol. 55 pp. 217-250.
Hawkins et al "Protein Nanoparticles As Drug Carriers in Clinical Medicine "Adv Drug Deliv Rev 2008 vol. 60 pp. 876-885.
Hinkle et al "Urocortin II Treatment Rduces Skeletal Muscle Mass and Function Loss During Atrophy and Increases Nonatrophying Skeletal Muscle Mass and Function" Endocrinology 2003 vol. 144(1) pp. 4939-4946.
Hixon et al Chemical Engineer 1990 pp. 94-103.
Hsu et al "Human Stresscopin and Stresscopin-Related Peptide Are Selective Ligands for the Type-2 Corticotropin-Releasing Hormone Receptor" Nat Med 2001 vol. 7(5) pp. 605-611.
Isfort et al "Modifications of the Human Urocortin 2 Peptide That Improve Pharmacological Properties" Peptides 2006 vol. 27 pp. 1806-1813.
Johnson "Preparation of Peptide and Protein Powders for Inhalation" Adv Drug Del Rev 1997 vol. 26 pp. 3-15.
Kaufman et al"Translational Efficiency of Polycistronic MRNA and Their Utilization to Express Heterologous Genes in Mammalian Cells" EMBO J. 1987 vol. 6(1) pp. 187-193.
Alitalo et al Synthetic Peptides in Biology and Medicine 1985 Kari Alitalo Paul Partanen Antti Vaheri Eds Elvesier Science Publishers 1985 pp. 29-57.
Kishimoto et al "Deletion of CRH2 Reveals an Anxiolyc Role for Corticotropin-Releasing Hormone Receptor-2" Nat Genet 2000 vol. 24 pp. 415-419.
Larsen et al Design and Application of Prodrugs Drug Design and Development Krogsgaard-Larsed et al. Eds Harwood Academic Publishers 1991, TOC and index only, 18 pages total.
Lewis et al "Identification of Urocortin III, an Additional Member of the Corticotropin-Releasing Factor (CRF) Family With Hight Affinity for the CRF2 Receptor" PNAS 2001 vol. 98(13) pp. 7570-7575.
Li et al "Urocortin III as Expressed in Pancreatic B-Cells and Stimulates Insulin and Glucagon Secretion" Endocrinology 2003 vol. 144(7) pp. 3216-3224.
Makrides et al "Strategies for Achieving High-Level Expression of Genes in *Excheridia coli*" Microbiol Rev 1996 vol. 60(3) pp. 512-538.
Remington's Pharmaceutical Sciences 1990 18th Ed Mack Publishing Easton PA, TOC and index only, 36 pages total.
McOmie J.F.W. Protective Groups in Organic Chemistry Plenum Press New York, NY 1973, pp. 416-418 only, index only.
Merrifield et al. "Solid Phase Peptide Synthesis. I. The Synthesis of a Tetrapeptide" Am Chem Soc 1963 vol. 15 pp. 2149-2154.

Moffatt et al "Activation of Corticotropin-Releasing Factor Receptor-2 Causes Bronchorelaxation and Inhibits Pulmonary Inflammation in Mice" The FASEB J 2006 vol. 20 pp. 1877-1879.
Moffatt et al "Activation of Corticotropin-Releasing Factor Receptor-2 Causes Bronchorelaxation and Inhibits Pulmonary Inflammation in Mice" The FASEB J 2006 vol. 20 pp. E1181-E1187.
Montalvo et al "Formation of Spherical Protein Nanoparticles Without Impacting Protein Integrity" Nanotechnology 2008 vol. 19 pp. 1-7.
Morrison et al "Transformation in *Escheria coli*: Cryogenic Preservaton of Competent Cells" J Bact 1977 vol. 132(1) pp. 349-351.
Mosbach et al "Formation of Proinsulin by Immobilized Bacillus Subtilis" Nature 1983 vol. 302(7) pp. 543-545.
Ohata et al "Effects of Urocortin 2 and 3 on Motor Activity and Food Intake in Rats" Peptides 2004 vol. 25 pp. 1703-1709.
Palva et al "Secretion of Interferon by Bacillus Subtilis" Gene 1983 vol. 22 pp. 229-235.
Parrots "Milling of Pharmaceutical Salts" Journal of Pharmaceutical Sciences 1974 vol. 63(6) pp. 813-829.
Pelham et al "An Efficient MRNA-Dependent Translation System From Reticulocyte Lysates" Eur J Biochem 1976 vol. 67 pp. 247-256.
Perry's Chemical Engineers Handbook 6th Ed. 1984 pp. 21-13-21-19.
Ripple et al "Powders" Pharmaceutical Sciences Remington 17th Ed pp. 1585-1594 1985.
Rademaker et al "Integrated Hemodynamic Hormonal and Renal Actions of Urocortin 2 in Normal and Paced Sheep" Circulation 2005 vol. 112 pp. 3624-3632.
Rademaker et al. "Urocortin 3: Haemodynamic Hormonal and Renal Effects in Experimental Heart Failure" Eur Heart J. 2006 vol. 27 pp. 2088-2098.
Ray et al "Production of Recombinant Salmon Calcitonin by in Vitro Amidation of an *Escheria coli* Produced Precurson Peptide" Nature Biotechnology 1993 vol. 11 pp. 64-70.
Remme et al "Guidelines for the Diagnosis and Treatment of Chronic Heart Failure" Eur Heart J 2001 vol. 22 pp. 1527-1560.
Roberts et al "Chemistry for Peptide and Protein Pegylation" Adv Drug Del Rev 2002 vol. 54 pp. 459-476.
Sambrook et al Molecular Cloning : A Laboratory Manual 1989 2nd Ed Cold Spring Harbor New York, TOC only, 29 pages.
Sambrook et al et al "Molecular Cloning: A Laboratory Manual" 1989 pp. 10.59 to 10.61.
Sambrook et al et al "Molecular Cloning: A Laboratory Manual" 1989 Chapters 16 vol. 2: pp. 16.3-16.81.
Sambrook et al et al "Molecular Cloning: A Laboratory Manual" 1989 Chapters 17 vol. 2, TOC and pp. 17.1-17.44.
Sangwan et al "Aerolized Protein Delivery in Asthma: Gamma Camera Analysis of Regional Deposition and Perfusion" J Aerosol Med 2001 vol. 14(2) pp. 185-195.
Seed "An LFA CDNA Encodes a Phospholipid-Linked Membrane Protein Homologous Ot Its Receptor CD2" Nature 1987 vol. 329(29) pp. 840.
Shan et al "Prodrug Strategies Based on Intramolecular Cyclization Reactions" J Pharm Sci 1997 vol. 86(7) pp. 765-767.
Stahl and Vermuth Eds. Handbook of Pharmaceutical Salts, Properties, Selection and Use 2002 Wiley-VCH and VHCA Zurich 2002, TOC only, 3 pages.
Stewart et al Solid Phase Peptide Synthesis Pierce Chemical Co Rockford IL 1984, TOC only, 7 pages total.
Tang et al "Exploring New Drugs for Heart Failure: The Case of Urocortin" Eur Heart J 2007 vol. 28 pp. 2561-2562.
Neurath et al The Proteins 1976 vol. II 3rd Hans Neurath Robert L. Hill Carol-Leigh Boeder Eds pp. 105-253.
Vale et al "Characterization of a 41-Residue Ovine Hypothalamic Peptide That Stimulates Secretion of Corticotropin and B-Endorphin" Science 1981 vol. 213 pp. 1394-1397.
Walsh et al Post-Translational Modification in the Context of Therapeutic Proteins' Nature Biotechnology 2006 vol. 24(10) pp. 1241-1252.
Zubay "In Vitro Synthesis of Protein in Microbial Systems" Annu Rev Genet 1973 vol. 7 pp. 267-287.

(56) References Cited

OTHER PUBLICATIONS

International Search Report for corresponding International Application PCT/US2010/055526 mailed on May 13, 2011, 6 pages.
Chandler Etal "Short-Term Treatment With Ranolazine Improves Mechanical Efficiency in Dogs With Chronic Heart Failure" Circ Res 2002 vol. 91 pp. 278-280.
Gardiner et al "A Comparison Between the Cardiovascular Actions of Urocortin 1 and Urocortin 2 (Stresscopin-Related Peptide) in Conscious Rats" The Journal of Pharm and Exp Therapeutics 2007 vol. 321(1) pp. 221-226.
Sabbah et al "Effects of Long-Term Monotherapy With Enalapril, Metropolol, and Digoxin on the Progression of Left Ventricular Dysfunction and Dilation in Dogs With Reduced Ejection Fraction" Circ 1994 vol. 89(6) pp. 2852-2859.
Sabbah et al "A Canine Model of Chronic Heart Failure Produced by Multiple Sequential Coronary Microembolizations" Am J Physiol 1991 vol. 260 pp. H1379-H1384.
Alitalo et al Synthetic Peptides in Biology and Medicine 1985 Kari Alitalo Paul Partanen Antti Vaheri Eds Elsevier Science Publishers 1985, TOC and index only, 11 pages total.
Partial International Search Report Annex to Form PC/ISA/206 for Corresponding PCT/US2009/063276 Mailed on Feb. 26, 2010.
Bailon et al "Polyethylene Glycol-Conjugated Pharmaceutical Proteins" PSTT 1998 vol. 1(8) pp. 352-356.
Clark-Curtiss et al "Analysis of Recombinant DNA Using *Escherichia coli* Minicells" Methods in Enzymology 1983 vol. 101 pp. 347-362.
Fishburn C. Simone "The Pharmacology of Pegylation: Balancing PD With PK to Generate Novel Therapeutics" J. Pharm Sci. 2008 vol. 97 pp. 4167-4183.
Hamidi et al "Pharmacokinetic Consequences of Pegylation" Drug Delivery 2006 vol. 13 pp. 399-409.
Harris et al "Effects of Pegylation on Pharmaceuticals" Nat Rev Drug Discov 2003 vol. 2 pp. 214-221.
Merrifield et al. "Solid Phase Peptide Synthesis. I. The Synthesis of a Tetrapeptide" Am Chem Soc 1963 vol. 85 pp. 2149-2154.
Bompadre et al., "Mechanism of G551D-CFTR (Cystic Fibrosis Transmembrane Conductance Regulator) Potentiation by a High Affinity ATP Analog*.", J. Bio. Chem., 2008, pp. 5364-5369, vol. 283(9).
Grace et al., "Structure of the N-Terminal Domain of a Type B1 G Ptotein-Coupled Receptor in Complex With a Peptide Ligand.", PNAS, 2007, pp. 4858-4863, vol. 104(2).
Gulyas et al., "Potent, structurally constrained agonists and competitive antagonists of corticotropin-releasing factor.", Proc. Natl. Acad. Sci., 1995, pp. 10575-10579, vol. 92.
Mickle et al., "Genotype-Phenotype Relationships in Cystic Fibrosis.", Inherited Disaeases of the Pancreas, Medical Clinics of North America, May 2000, pp. 597-607, vol. 84(3).
Khan et al., "Urocortin in cardiovascular disease: pathophysiology and therapeutic potential," Drug Discovery Today: Therapeutic Strategies, 2004; 1(2): pp. 163-168.
Zobel et al., "Effects of the high-affinity corticotropin-releasing hormone receptor 1 antagonist R121919 in major depression: the first 20 patients treated," J. of Psychiatric Research, 2000; 34: pp. 171-181.

\* cited by examiner

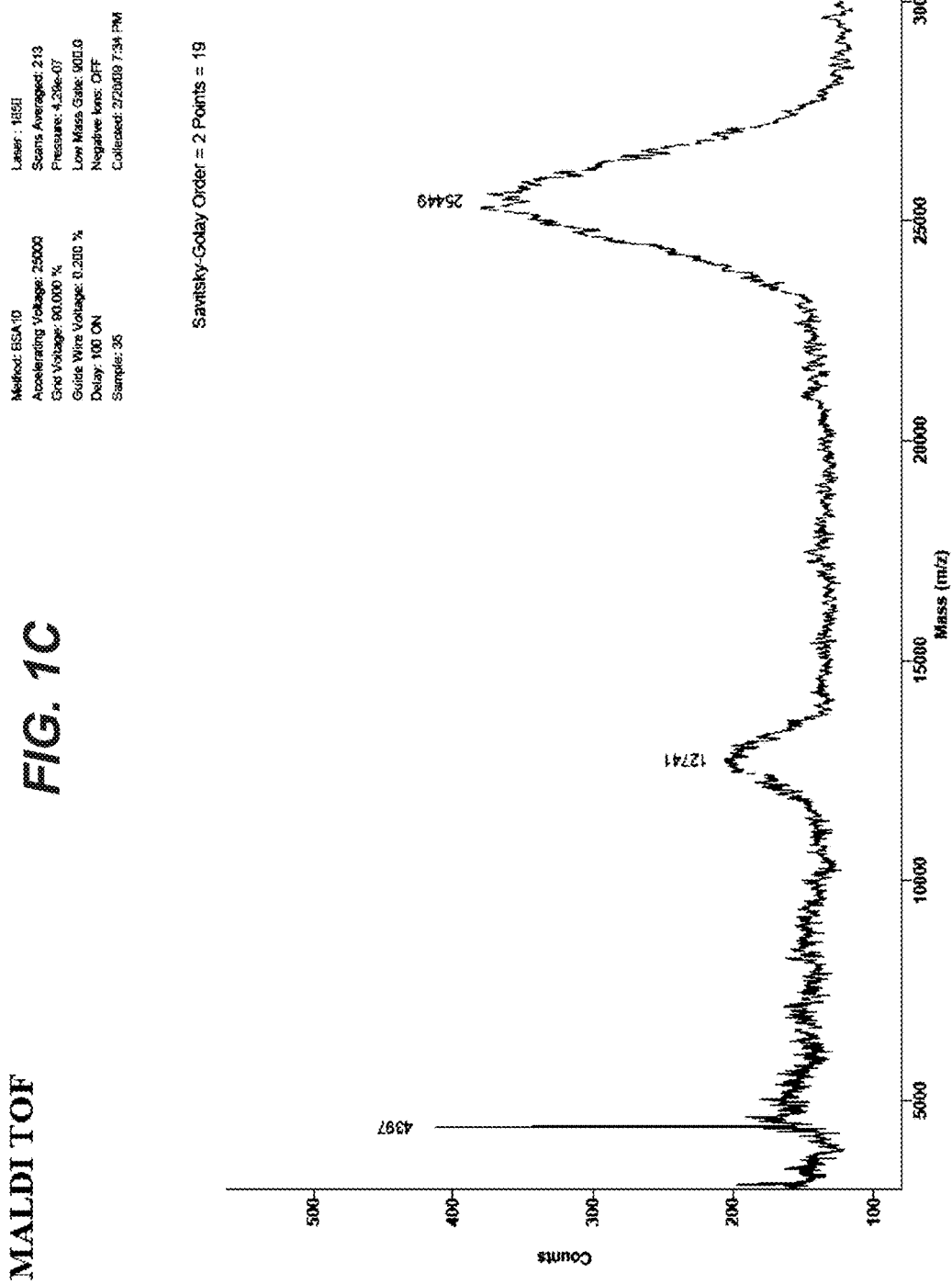

FIG. 6
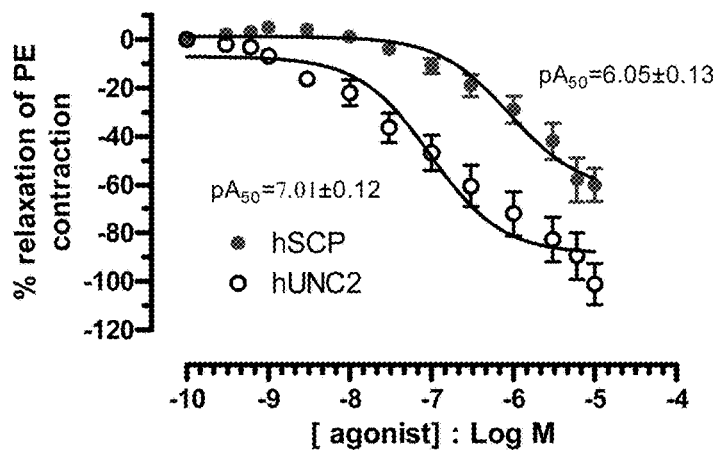
FIG. 7
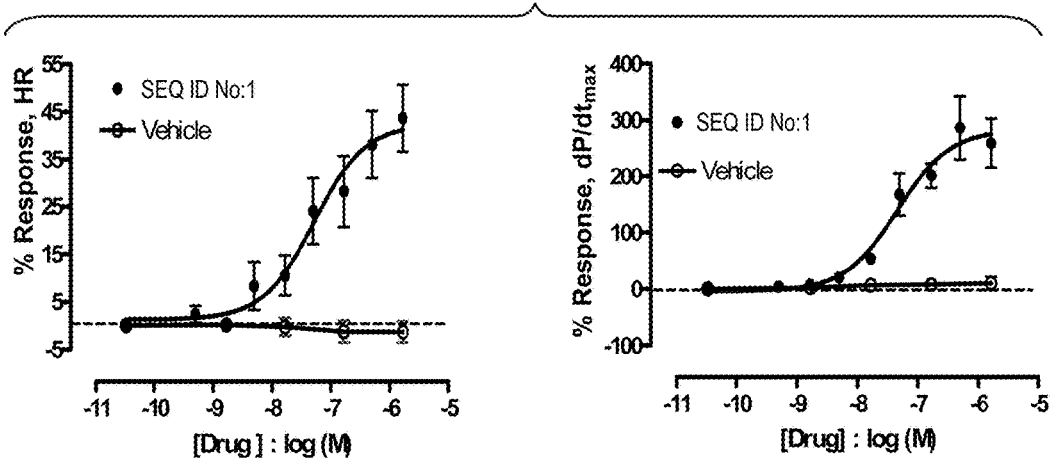
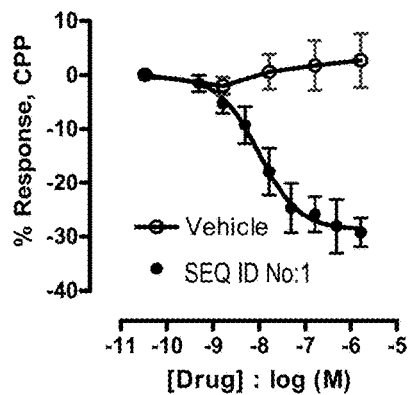

SEQUENCE LISTING

<160> NUMBER OF SEQ ID NOS: 123

<210> SEQ ID NO 1
<211> LENGTH: 40
<212> TYPE: PRT
<213> ORGANISM: Homo sapiens
<220> FEATURE:
<221> NAME/KEY: MOD_RES
<222> LOCATION: (40)..(40)
<223> OTHER INFORMATION: AMIDATION

<400> SEQUENCE: 1

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 2

Cys Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 3

Thr Cys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)

-continued

<223> OTHER INFORMATION: AMIDATION

<400> SEQUENCE: 4

Thr Lys Cys Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 5

Thr Lys Phe Cys Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 6

Thr Lys Phe Thr Cys Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 7
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 7

Thr Lys Phe Thr Leu Cys Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 8
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 8

Thr Lys Phe Thr Leu Ser Cys Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 9
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 9

Thr Lys Phe Thr Leu Ser Leu Cys Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 10
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 10

Thr Lys Phe Thr Leu Ser Leu Asp Cys Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 11
<211> LENGTH: 40
<212> TYPE: PRT
<213> ORGANISM: Artificial Sequence
<220> FEATURE:
<223> OTHER INFORMATION: Synthetic peptide

```
<220> FEATURE:
<221> NAME/KEY: MOD_RES
<222> LOCATION: (40)..(40)
<223> OTHER INFORMATION: AMIDATION

<400> SEQUENCE: 11

Thr Lys Phe Thr Leu Ser Leu Asp Val Cys Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 12
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 12

Thr Lys Phe Thr Leu Ser Leu Asp Val Pro Cys Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 13
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 13

Thr Lys Phe Thr Leu Ser Leu Asp Val Pro Thr Cys Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 14

Thr Lys Phe Thr Leu Ser Leu Asp Val Pro Thr Asn Cys Met Asn Leu
1               5                   10                  15
```

Leu Phe Asn Ile Ala Lys Ala Lys Asn Leu Arg Ala Gln Ala Ala
            20                  25                  30

Asn Ala His Leu Met Ala Gln Ile
            35                  40

<210> SEQ ID NO 15
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 15

Thr Lys Phe Thr Leu Ser Leu Asp Val Pro Thr Asn Ile Cys Asn Leu
1               5                   10                  15

Leu Phe Asn Ile Ala Lys Ala Lys Asn Leu Arg Ala Gln Ala Ala
            20                  25                  30

Asn Ala His Leu Met Ala Gln Ile
            35                  40

<210> SEQ ID NO 16
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 16

Thr Lys Phe Thr Leu Ser Leu Asp Val Pro Thr Asn Ile Met Cys Leu
1               5                   10                  15

Leu Phe Asn Ile Ala Lys Ala Lys Asn Leu Arg Ala Gln Ala Ala
            20                  25                  30

Asn Ala His Leu Met Ala Gln Ile
            35                  40

<210> SEQ ID NO 17
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 17

Thr Lys Phe Thr Leu Ser Leu Asp Val Pro Thr Asn Ile Met Asn Cys
1               5                   10                  15

Leu Phe Asn Ile Ala Lys Ala Lys Asn Leu Arg Ala Gln Ala Ala
            20                  25                  30

Asn Ala His Leu Met Ala Gln Ile
            35                  40

<210> SEQ ID NO 18
<211> LENGTH: 40
<212> TYPE: PRT

<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 18

Thr Lys Phe Thr Leu Ser Leu Asp Val Pro Thr Asn Ile Met Asn Leu
1               5                   10                  15

Cys Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 19
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 19

Thr Lys Phe Thr Leu Ser Leu Asp Val Pro Thr Asn Ile Met Asn Leu
1               5                   10                  15

Leu Cys Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 20
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 20

Thr Lys Phe Thr Leu Ser Leu Asp Val Pro Thr Asn Ile Met Asn Leu
1               5                   10                  15

Leu Phe Cys Ile Ala Lys Ala Lys Asn Leu Arg Ala Gln Ala Ala Ala
            20                  25                  30

Asn Ala His Leu Met Ala Gln Ile
        35                  40

<210> SEQ ID NO 21
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 21

Thr Lys Phe Thr Leu Ser Leu Asp Val Pro Thr Asn Ile Met Asn Leu
1               5                   10                  15

Leu Phe Asn Cys Ala Lys Ala Lys Asn Leu Arg Ala Gln Ala Ala Ala
            20                  25                  30

Asn Ala His Leu Met Ala Gln Ile
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 22

Thr Lys Phe Thr Leu Ser Leu Asp Val Pro Thr Asn Ile Met Asn Leu
1               5                   10                  15

Leu Phe Asn Ile Cys Lys Ala Lys Asn Leu Arg Ala Gln Ala Ala Ala
            20                  25                  30

Asn Ala His Leu Met Ala Gln Ile
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 23

Thr Lys Phe Thr Leu Ser Leu Asp Val Pro Thr Asn Ile Met Asn Leu
1               5                   10                  15

Leu Phe Asn Ile Ala Cys Ala Lys Asn Leu Arg Ala Gln Ala Ala Ala
            20                  25                  30

Asn Ala His Leu Met Ala Gln Ile
        35                  40

<210> SEQ ID NO 24
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 24

Thr Lys Phe Thr Leu Ser Leu Asp Val Pro Thr Asn Ile Met Asn Leu
1               5                   10                  15

Leu Phe Asn Ile Ala Lys Cys Lys Asn Leu Arg Ala Gln Ala Ala Ala
            20                  25                  30

Asn Ala His Leu Met Ala Gln Ile
        35                  40

```
<210> SEQ ID NO 25
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 25

Thr Lys Phe Thr Leu Ser Leu Asp Val Pro Thr Asn Ile Met Asn Leu
1               5                   10                  15

Leu Phe Asn Ile Ala Lys Ala Cys Asn Leu Arg Ala Gln Ala Ala Ala
            20                  25                  30

Asn Ala His Leu Met Ala Gln Ile
        35                  40

<210> SEQ ID NO 26
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 26

Thr Lys Phe Thr Leu Ser Leu Asp Val Pro Thr Asn Ile Met Asn Leu
1               5                   10                  15

Leu Phe Asn Ile Ala Lys Ala Lys Cys Leu Arg Ala Gln Ala Ala Ala
            20                  25                  30

Asn Ala His Leu Met Ala Gln Ile
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 27

Thr Lys Phe Thr Leu Ser Leu Asp Val Pro Thr Asn Ile Met Asn Leu
1               5                   10                  15

Leu Phe Asn Ile Ala Lys Ala Lys Asn Cys Arg Ala Gln Ala Ala Ala
            20                  25                  30

Asn Ala His Leu Met Ala Gln Ile
        35                  40

<210> SEQ ID NO 28
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
```

```
<400> SEQUENCE: 28

Thr Lys Phe Thr Leu Ser Leu Asp Val Pro Thr Asn Ile Met Asn Leu
1               5                   10                  15

Leu Phe Asn Ile Ala Lys Ala Lys Asn Leu Cys Ala Gln Ala Ala Ala
            20                  25                  30

Asn Ala His Leu Met Ala Gln Ile
        35                  40

<210> SEQ ID NO 29
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 29

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
            20                  25                  30

Asn Ala His Leu Met Ala Gln Ile
        35                  40

<210> SEQ ID NO 30
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 30

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Cys Ala Ala Ala
            20                  25                  30

Asn Ala His Leu Met Ala Gln Ile
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 31

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Cys Ala Ala
            20                  25                  30

Asn Ala His Leu Met Ala Gln Ile
```

<210> SEQ ID NO 32
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 32

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Cys Ala
            20                  25                  30

Asn Ala His Leu Met Ala Gln Ile
            35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 33

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Cys
            20                  25                  30

Asn Ala His Leu Met Ala Gln Ile
            35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 34

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Cys Ala His Leu Met Ala Gln Ile
            35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic peptide
<220> FEATURE:

<221> NAME/KEY: MOD_RES
<222> LOCATION: (40)..(40)
<223> OTHER INFORMATION: AMIDATION

<400> SEQUENCE: 35

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Cys His Leu Met Ala Gln Ile
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 36

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala Cys Leu Met Ala Gln Ile
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 37

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Cys Met Ala Gln Ile
        35                  40

<210> SEQ ID NO 38
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 38

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala

Asn Ala His Leu Cys Ala Gln Ile
        35                  40

<210> SEQ ID NO 39
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 39

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Cys Gln Ile
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 40

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Cys Ile
        35                  40

<210> SEQ ID NO 41
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION

<400> SEQUENCE: 41

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Cys
        35                  40

<210> SEQ ID NO 42
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (40)..(40)
<223> OTHER INFORMATION: Cys-NES

<400> SEQUENCE: 42

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Cys
        35                  40

<210> SEQ ID NO 43
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (35)..(35)
<223> OTHER INFORMATION: Cys-NES

<400> SEQUENCE: 43

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala Cys Leu Met Ala Gln Ile
        35                  40

<210> SEQ ID NO 44
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (33)..(33)
<223> OTHER INFORMATION: Cys-NES

<400> SEQUENCE: 44

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Cys Ala His Leu Met Ala Gln Ile
        35                  40

<210> SEQ ID NO 45
<211> LENGTH: 40

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (32)..(32)
<223> OTHER INFORMATION: Cys-NES

<400> SEQUENCE: 45

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Cys
            20                  25                  30

Asn Ala His Leu Met Ala Gln Ile
        35                  40

<210> SEQ ID NO 46
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (31)..(31)
<223> OTHER INFORMATION: Cys-NES

<400> SEQUENCE: 46

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Cys Ala
            20                  25                  30

Asn Ala His Leu Met Ala Gln Ile
        35                  40

<210> SEQ ID NO 47
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES

<400> SEQUENCE: 47

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
            20                  25                  30

Asn Ala His Leu Met Ala Gln Ile
        35                  40
```

```
<210> SEQ ID NO 48
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (26)..(26)
<223> OTHER INFORMATION: Cys-NES

<400> SEQUENCE: 48

Thr Lys Phe Thr Leu Ser Leu Asp Val Pro Thr Asn Ile Met Asn Leu
1               5                   10                  15

Leu Phe Asn Ile Ala Lys Ala Lys Asn Cys Arg Ala Gln Ala Ala Ala
            20                  25                  30

Asn Ala His Leu Met Ala Gln Ile
        35                  40

<210> SEQ ID NO 49
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (25)..(25)
<223> OTHER INFORMATION: Cys-NES

<400> SEQUENCE: 49

Thr Lys Phe Thr Leu Ser Leu Asp Val Pro Thr Asn Ile Met Asn Leu
1               5                   10                  15

Leu Phe Asn Ile Ala Lys Ala Lys Cys Leu Arg Ala Gln Ala Ala Ala
            20                  25                  30

Asn Ala His Leu Met Ala Gln Ile
        35                  40

<210> SEQ ID NO 50
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (24)..(24)
<223> OTHER INFORMATION: Cys-NES

<400> SEQUENCE: 50

Thr Lys Phe Thr Leu Ser Leu Asp Val Pro Thr Asn Ile Met Asn Leu
1               5                   10                  15

Leu Phe Asn Ile Ala Lys Ala Cys Asn Leu Arg Ala Gln Ala Ala Ala
            20                  25                  30

Asn Ala His Leu Met Ala Gln Ile
        35                  40
```

```
<210> SEQ ID NO 51
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (20)..(20)
<223> OTHER INFORMATION: Cys-NES

<400> SEQUENCE: 51

Thr Lys Phe Thr Leu Ser Leu Asp Val Pro Thr Asn Ile Met Asn Leu
1               5                   10                  15

Leu Phe Asn Cys Ala Lys Ala Lys Asn Leu Arg Ala Gln Ala Ala Ala
            20                  25                  30

Asn Ala His Leu Met Ala Gln Ile
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (19)..(19)
<223> OTHER INFORMATION: Cys-NES

<400> SEQUENCE: 52

Thr Lys Phe Thr Leu Ser Leu Asp Val Pro Thr Asn Ile Met Asn Leu
1               5                   10                  15

Leu Phe Cys Ile Ala Lys Ala Lys Asn Leu Arg Ala Gln Ala Ala Ala
            20                  25                  30

Asn Ala His Leu Met Ala Gln Ile
        35                  40

<210> SEQ ID NO 53
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (17)..(17)
<223> OTHER INFORMATION: Cys-NES

<400> SEQUENCE: 53

Thr Lys Phe Thr Leu Ser Leu Asp Val Pro Thr Asn Ile Met Asn Leu
1               5                   10                  15

Cys Phe Asn Ile Ala Lys Ala Lys Asn Leu Arg Ala Gln Ala Ala Ala
            20                  25                  30
```

-continued

Asn Ala His Leu Met Ala Gln Ile
        35                  40

<210> SEQ ID NO 54
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (16)..(16)
<223> OTHER INFORMATION: Cys-NES

<400> SEQUENCE: 54

Thr Lys Phe Thr Leu Ser Leu Asp Val Pro Thr Asn Ile Met Asn Cys
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 55
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (1)..(1)
<223> OTHER INFORMATION: Cys-NES-Peg_MW20000

<400> SEQUENCE: 55

Cys Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 56
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (2)..(2)
<223> OTHER INFORMATION: Cys-NES-Peg_MW20000

<400> SEQUENCE: 56

Thr Cys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala

```
                    20                  25                  30

Asn Ala His Leu Met Ala Gln Ile
        35                  40

<210> SEQ ID NO 57
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (3)..(3)
<223> OTHER INFORMATION: Cys-NES-Peg_MW20000

<400> SEQUENCE: 57

Thr Lys Cys Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 58
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (4)..(4)
<223> OTHER INFORMATION: Cys-NES-Peg_MW20000

<400> SEQUENCE: 58

Thr Lys Phe Cys Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (5)..(5)
<223> OTHER INFORMATION: Cys-NES-Peg_MW20000

<400> SEQUENCE: 59

Thr Lys Phe Thr Cys Ser Leu Asp Val Pro Thr Asn Ile Met Asn Leu
1               5                   10                  15
```

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (6)..(6)
<223> OTHER INFORMATION: Cys-NES-Peg_MW20000

<400> SEQUENCE: 60

Thr Lys Phe Thr Leu Cys Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (7)..(7)
<223> OTHER INFORMATION: Cys-NES-Peg_MW20000

<400> SEQUENCE: 61

Thr Lys Phe Thr Leu Ser Cys Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (8)..(8)
<223> OTHER INFORMATION: Cys-NES-Peg_MW20000

<400> SEQUENCE: 62

-continued

Thr Lys Phe Thr Leu Ser Leu Cys Val Pro Thr Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
            35                  40

<210> SEQ ID NO 63
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (9)..(9)
<223> OTHER INFORMATION: Cys-NES-Peg_MW20000

<400> SEQUENCE: 63

Thr Lys Phe Thr Leu Ser Leu Asp Cys Pro Thr Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
            35                  40

<210> SEQ ID NO 64
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (10)..(10)
<223> OTHER INFORMATION: Cys-NES-Peg_MW20000

<400> SEQUENCE: 64

Thr Lys Phe Thr Leu Ser Leu Asp Val Cys Thr Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
            35                  40

<210> SEQ ID NO 65
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (11)..(11)
<223> OTHER INFORMATION: Cys-NES-Peg_MW20000

<400> SEQUENCE: 65

Thr Lys Phe Thr Leu Ser Leu Asp Val Pro Cys Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
        35                  40

<210> SEQ ID NO 66
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (12)..(12)
<223> OTHER INFORMATION: Cys-NES-Peg_MW20000

<400> SEQUENCE: 66

Thr Lys Phe Thr Leu Ser Leu Asp Val Pro Thr Cys Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
        35                  40

<210> SEQ ID NO 67
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (13)..(13)
<223> OTHER INFORMATION: Cys-NES-Peg_MW20000

<400> SEQUENCE: 67

Thr Lys Phe Thr Leu Ser Leu Asp Val Pro Thr Asn Cys Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile
        35                  40

<210> SEQ ID NO 68
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (14)..(14)

<223> OTHER INFORMATION: Cys-NES-Peg_MW20000

<400> SEQUENCE: 68

Thr Lys Phe Thr Leu Ser Leu Asp Val Pro Thr Asn Ile Cys Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 69
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (15)..(15)
<223> OTHER INFORMATION: Cys-NES-Peg_MW20000

<400> SEQUENCE: 69

Thr Lys Phe Thr Leu Ser Leu Asp Val Pro Thr Asn Ile Met Cys Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (16)..(16)
<223> OTHER INFORMATION: Cys-NES-Peg_MW20000

<400> SEQUENCE: 70

Thr Lys Phe Thr Leu Ser Leu Asp Val Pro Thr Asn Ile Met Asn Cys
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 71
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:

<221> NAME/KEY: MOD_RES
<222> LOCATION: (17)..(17)
<223> OTHER INFORMATION: Cys-NES-Peg_MW20000

<400> SEQUENCE: 71

Thr Lys Phe Thr Leu Ser Leu Asp Val Pro Thr Asn Ile Met Asn Leu
1               5                   10                  15
Cys Phe Asn Ile Ala Lys Ala Lys Asn Leu Arg Ala Gln Ala Ala Ala
                20                  25                  30
Asn Ala His Leu Met Ala Gln Ile
            35                  40

<210> SEQ ID NO 72
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (18)..(18)
<223> OTHER INFORMATION: Cys-NES-Peg_MW20000

<400> SEQUENCE: 72

Thr Lys Phe Thr Leu Ser Leu Asp Val Pro Thr Asn Ile Met Asn Leu
1               5                   10                  15
Leu Cys Asn Ile Ala Lys Ala Lys Asn Leu Arg Ala Gln Ala Ala Ala
                20                  25                  30
Asn Ala His Leu Met Ala Gln Ile
            35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (19)..(19)
<223> OTHER INFORMATION: Cys-NES-Peg_MW20000

<400> SEQUENCE: 73

Thr Lys Phe Thr Leu Ser Leu Asp Val Pro Thr Asn Ile Met Asn Leu
1               5                   10                  15
Leu Phe Cys Ile Ala Lys Ala Lys Asn Leu Arg Ala Gln Ala Ala Ala
                20                  25                  30
Asn Ala His Leu Met Ala Gln Ile
            35                  40

<210> SEQ ID NO 74
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)

```
<223> OTHER INFORMATION: AMIDATION
<220> FEATURE:
<221> NAME/KEY: MOD_RES
<222> LOCATION: (20)..(20)
<223> OTHER INFORMATION: Cys-NES-Peg_MW20000

<400> SEQUENCE: 74

Thr Lys Phe Thr Leu Ser Leu Asp Val Pro Thr Asn Ile Met Asn Leu
1               5                   10                  15

Leu Phe Asn Cys Ala Lys Ala Lys Asn Leu Arg Ala Gln Ala Ala Ala
            20                  25                  30

Asn Ala His Leu Met Ala Gln Ile
        35                  40

<210> SEQ ID NO 75
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (21)..(21)
<223> OTHER INFORMATION: Cys-NES-Peg_MW20000

<400> SEQUENCE: 75

Thr Lys Phe Thr Leu Ser Leu Asp Val Pro Thr Asn Ile Met Asn Leu
1               5                   10                  15

Leu Phe Asn Ile Cys Lys Ala Lys Asn Leu Arg Ala Gln Ala Ala Ala
            20                  25                  30

Asn Ala His Leu Met Ala Gln Ile
        35                  40

<210> SEQ ID NO 76
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (22)..(22)
<223> OTHER INFORMATION: Cys-NES-Peg_MW20000

<400> SEQUENCE: 76

Thr Lys Phe Thr Leu Ser Leu Asp Val Pro Thr Asn Ile Met Asn Leu
1               5                   10                  15

Leu Phe Asn Ile Ala Cys Ala Lys Asn Leu Arg Ala Gln Ala Ala Ala
            20                  25                  30

Asn Ala His Leu Met Ala Gln Ile
        35                  40

<210> SEQ ID NO 77
<211> LENGTH: 40
<212> TYPE: PRT
<213> ORGANISM: Artificial Sequence
<220> FEATURE:
<223> OTHER INFORMATION: Synthetic peptide
<220> FEATURE:
```

<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (23)..(23)
<223> OTHER INFORMATION: Cys-NES-Peg_MW20000

<400> SEQUENCE: 77

Thr Lys Phe Thr Leu Ser Leu Asp Val Pro Thr Asn Ile Met Asn Leu
1               5                   10                  15

Leu Phe Asn Ile Ala Lys Cys Lys Asn Leu Arg Ala Gln Ala Ala Ala
            20                  25                  30

Asn Ala His Leu Met Ala Gln Ile
        35                  40

<210> SEQ ID NO 78
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (24)..(24)
<223> OTHER INFORMATION: Cys-NES-Peg_MW20000

<400> SEQUENCE: 78

Thr Lys Phe Thr Leu Ser Leu Asp Val Pro Thr Asn Ile Met Asn Leu
1               5                   10                  15

Leu Phe Asn Ile Ala Lys Ala Cys Asn Leu Arg Ala Gln Ala Ala Ala
            20                  25                  30

Asn Ala His Leu Met Ala Gln Ile
        35                  40

<210> SEQ ID NO 79
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (25)..(25)
<223> OTHER INFORMATION: Cys-NES-Peg_MW20000

<400> SEQUENCE: 79

Thr Lys Phe Thr Leu Ser Leu Asp Val Pro Thr Asn Ile Met Asn Leu
1               5                   10                  15

Leu Phe Asn Ile Ala Lys Ala Lys Cys Leu Arg Ala Gln Ala Ala Ala
            20                  25                  30

Asn Ala His Leu Met Ala Gln Ile
        35                  40

<210> SEQ ID NO 80
<211> LENGTH: 40
<212> TYPE: PRT
<213> ORGANISM: Artificial Sequence
<220> FEATURE:

```
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (26)..(26)
<223> OTHER INFORMATION: Cys-NES-Peg_MW20000

<400> SEQUENCE: 80

Thr Lys Phe Thr Leu Ser Leu Asp Val Pro Thr Asn Ile Met Asn Leu
1               5                   10                  15

Leu Phe Asn Ile Ala Lys Ala Lys Asn Cys Arg Ala Gln Ala Ala Ala
            20                  25                  30

Asn Ala His Leu Met Ala Gln Ile
        35                  40

<210> SEQ ID NO 81
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (27)..(27)
<223> OTHER INFORMATION: Cys-NES-Peg_MW20000

<400> SEQUENCE: 81

Thr Lys Phe Thr Leu Ser Leu Asp Val Pro Thr Asn Ile Met Asn Leu
1               5                   10                  15

Leu Phe Asn Ile Ala Lys Ala Lys Asn Leu Cys Ala Gln Ala Ala Ala
            20                  25                  30

Asn Ala His Leu Met Ala Gln Ile
        35                  40

<210> SEQ ID NO 82
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW20000

<400> SEQUENCE: 82

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
            20                  25                  30

Asn Ala His Leu Met Ala Gln Ile
        35                  40

<210> SEQ ID NO 83
<211> LENGTH: 40
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (29)..(29)
<223> OTHER INFORMATION: Cys-NES-Peg_MW20000

<400> SEQUENCE: 83

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Cys Ala Ala Ala
            20                  25                  30

Asn Ala His Leu Met Ala Gln Ile
        35                  40

<210> SEQ ID NO 84
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (30)..(30)
<223> OTHER INFORMATION: Cys-NES-Peg_MW20000

<400> SEQUENCE: 84

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Cys Ala Ala
            20                  25                  30

Asn Ala His Leu Met Ala Gln Ile
        35                  40

<210> SEQ ID NO 85
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (31)..(31)
<223> OTHER INFORMATION: Cys-NES-Peg_MW20000

<400> SEQUENCE: 85

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Cys Ala
            20                  25                  30

Asn Ala His Leu Met Ala Gln Ile
        35                  40

<210> SEQ ID NO 86
```

```
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (32)..(32)
<223> OTHER INFORMATION: Cys-NES-Peg_MW20000

<400> SEQUENCE: 86

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Cys
            20                  25                  30

Asn Ala His Leu Met Ala Gln Ile
        35                  40

<210> SEQ ID NO 87
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (33)..(33)
<223> OTHER INFORMATION: Cys-NES-Peg_MW20000

<400> SEQUENCE: 87

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Cys Ala His Leu Met Ala Gln Ile
        35                  40

<210> SEQ ID NO 88
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (34)..(34)
<223> OTHER INFORMATION: Cys-NES-Peg_MW20000

<400> SEQUENCE: 88

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Cys His Leu Met Ala Gln Ile
        35                  40
```

```
<210> SEQ ID NO 89
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (35)..(35)
<223> OTHER INFORMATION: Cys-NES-Peg_MW20000

<400> SEQUENCE: 89

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala Cys Leu Met Ala Gln Ile
        35                  40

<210> SEQ ID NO 90
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (36)..(36)
<223> OTHER INFORMATION: Cys-NES-Peg_MW20000

<400> SEQUENCE: 90

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Cys Met Ala Gln Ile
        35                  40

<210> SEQ ID NO 91
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (37)..(37)
<223> OTHER INFORMATION: Cys-NES-Peg_MW20000

<400> SEQUENCE: 91

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Cys Ala Gln Ile
```

<210> SEQ ID NO 92
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (38)..(38)
<223> OTHER INFORMATION: Cys-NES-Peg_MW20000

<400> SEQUENCE: 92

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Cys Gln Ile
        35                  40

<210> SEQ ID NO 93
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (39)..(39)
<223> OTHER INFORMATION: Cys-NES-Peg_MW20000

<400> SEQUENCE: 93

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Cys Ile
        35                  40

<210> SEQ ID NO 94
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (40)..(40)
<223> OTHER INFORMATION: Cys-NES-Peg_MW20000

<400> SEQUENCE: 94

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

```
Asn Ala His Leu Met Ala Gln Cys
        35                  40

<210> SEQ ID NO 95
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW2000

<400> SEQUENCE: 95

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
            20                  25                  30

Asn Ala His Leu Met Ala Gln Ile
        35                  40

<210> SEQ ID NO 96
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW5000

<400> SEQUENCE: 96

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
            20                  25                  30

Asn Ala His Leu Met Ala Gln Ile
        35                  40

<210> SEQ ID NO 97
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW12000

<400> SEQUENCE: 97

Thr Lys Phe Thr Leu Ser Leu Asp Val Pro Thr Asn Ile Met Asn Leu
1               5                   10                  15
```

Leu Phe Asn Ile Ala Lys Ala Lys Asn Leu Arg Cys Gln Ala Ala
            20                  25                  30

Asn Ala His Leu Met Ala Gln Ile
        35                  40

<210> SEQ ID NO 98
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW2000-NEM

<400> SEQUENCE: 98

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala
            20                  25                  30

Asn Ala His Leu Met Ala Gln Ile
        35                  40

<210> SEQ ID NO 99
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW30000

<400> SEQUENCE: 99

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala
            20                  25                  30

Asn Ala His Leu Met Ala Gln Ile
        35                  40

<210> SEQ ID NO 100
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW40000

<400> SEQUENCE: 100

Thr Lys Phe Thr Leu Ser Leu Asp Val Pro Thr Asn Ile Met Asn Leu

```
                1               5                  10                 15
Leu Phe Asn Ile Ala Lys Ala Lys Asn Leu Arg Cys Gln Ala Ala Ala
                        20                 25                 30

Asn Ala His Leu Met Ala Gln Ile
            35                 40

<210> SEQ ID NO 101
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-NES-Peg_MW40000_Branched

<400> SEQUENCE: 101

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
                        20                  25                  30

Asn Ala His Leu Met Ala Gln Ile
            35                  40

<210> SEQ ID NO 102
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-IA-Peg_MW20000

<400> SEQUENCE: 102

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala Ala
                        20                  25                  30

Asn Ala His Leu Met Ala Gln Ile
            35                  40

<210> SEQ ID NO 103
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-IA-Peg_MW30000

<400> SEQUENCE: 103
```

```
Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala
            20                  25                  30

Asn Ala His Leu Met Ala Gln Ile
            35                  40

<210> SEQ ID NO 104
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (28)..(28)
<223> OTHER INFORMATION: Cys-IA-Peg_MW40000

<400> SEQUENCE: 104

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Cys Gln Ala Ala
            20                  25                  30

Asn Ala His Leu Met Ala Gln Ile
            35                  40

<210> SEQ ID NO 105
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (12)..(12)
<223> OTHER INFORMATION: Cys-IA-Peg_MW20000

<400> SEQUENCE: 105

Thr Lys Phe Thr Leu Ser Leu Asp Val Pro Thr Cys Ile Met Asn Leu
1               5                   10                  15

Leu Phe Asn Ile Ala Lys Ala Lys Asn Leu Arg Ala Gln Ala Ala
            20                  25                  30

Asn Ala His Leu Met Ala Gln Ile
            35                  40

<210> SEQ ID NO 106
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (40)..(40)
<223> OTHER INFORMATION: AMIDATION
<220> FEATURE:
<221> NAME/KEY: MOD_RES
<222> LOCATION: (35)..(35)
<223> OTHER INFORMATION: Cys-IA-Peg_MW20000
```

<400> SEQUENCE: 106

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala Cys Leu Met Ala Gln Ile
        35                  40

<210> SEQ ID NO 107
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (39)..(39)
<223> OTHER INFORMATION: AMIDATION

<400> SEQUENCE: 107

Lys Phe Thr Leu Ser Leu Asp Val Pro Thr Asn Ile Met Asn Leu Leu
1               5                   10                  15

Phe Asn Ile Ala Lys Ala Lys Asn Leu Arg Ala Gln Ala Ala Ala Asn
            20                  25                  30

Ala His Leu Met Ala Gln Ile
        35

<210> SEQ ID NO 108
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (37)..(37)
<223> OTHER INFORMATION: AMIDATION

<400> SEQUENCE: 108

Thr Leu Ser Leu Asp Val Pro Thr Asn Ile Met Asn Leu Leu Phe Asn
1               5                   10                  15

Ile Ala Lys Ala Lys Asn Leu Arg Ala Gln Ala Ala Ala Asn Ala His
            20                  25                  30

Leu Met Ala Gln Ile
        35

<210> SEQ ID NO 109
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (36)..(36)
<223> OTHER INFORMATION: AMIDATION

<400> SEQUENCE: 109

Leu Ser Leu Asp Val Pro Thr Asn Ile Met Asn Leu Leu Phe Asn Ile
1               5                   10                  15

Ala Lys Ala Lys Asn Leu Arg Ala Gln Ala Ala Ala Asn Ala His Leu
            20                  25                  30

Met Ala Gln Ile

<210> SEQ ID NO 110
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (35)..(35)
<223> OTHER INFORMATION: AMIDATION

<400> SEQUENCE: 110

```
Ser Leu Asp Val Pro Thr Asn Ile Met Asn Leu Leu Phe Asn Ile Ala
1               5                   10                  15

Lys Ala Lys Asn Leu Arg Ala Gln Ala Ala Ala Asn Ala His Leu Met
            20                  25                  30

Ala Gln Ile
        35
```

<210> SEQ ID NO 111
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (34)..(34)
<223> OTHER INFORMATION: AMIDATION

<400> SEQUENCE: 111

```
Leu Asp Val Pro Thr Asn Ile Met Asn Leu Leu Phe Asn Ile Ala Lys
1               5                   10                  15

Ala Lys Asn Leu Arg Ala Gln Ala Ala Ala Asn Ala His Leu Met Ala
            20                  25                  30

Gln Ile
```

<210> SEQ ID NO 112
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (33)..(33)
<223> OTHER INFORMATION: AMIDATION

<400> SEQUENCE: 112

```
Asp Val Pro Thr Asn Ile Met Asn Leu Leu Phe Asn Ile Ala Lys Ala
1               5                   10                  15

Lys Asn Leu Arg Ala Gln Ala Ala Ala Asn Ala His Leu Met Ala Gln
            20                  25                  30

Ile
```

<210> SEQ ID NO 113
<211> LENGTH: 40
<212> TYPE: PRT
<213> ORGANISM: Homo sapiens

<400> SEQUENCE: 113

```
Thr Lys Phe Thr Leu Ser Leu Asp Val Pro Thr Asn Ile Met Asn Leu
1               5                   10                  15
```

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 114
<211> LENGTH: 40
<212> TYPE: PRT
<213> ORGANISM: Rattus norvegicus
<220> FEATURE:
<221> NAME/KEY: MOD_RES
<222> LOCATION: (40)..(40)
<223> OTHER INFORMATION: AMIDATION

<400> SEQUENCE: 114

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 115
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 115

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 116
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 116

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 117
<211> LENGTH: 43
<212> TYPE: PRT
<213> ORGANISM: Homo sapiens
<220> FEATURE:
<221> NAME/KEY: MOD_RES
<222> LOCATION: (43)..(43)
<223> OTHER INFORMATION: AMIDATION

<400> SEQUENCE: 117

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
            20                  25                  30

Ala Thr Thr Asn Ala Arg Ile Leu Ala Arg Val
        35                  40

<210> SEQ ID NO 118
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (30)..(30)
<223> OTHER INFORMATION: AMIDATION

<400> SEQUENCE: 118

Phe His Leu Leu Arg Lys Met Ile Glu Ile Glu Lys Gln Glu Lys Glu
1               5                   10                  15

Lys Gln Gln Ala Ala Asn Asn Arg Leu Leu Leu Asp Thr Ile
            20                  25                  30

<210> SEQ ID NO 119
<211> LENGTH: 36
<212> TYPE: PRT
<213> ORGANISM: Artificial Sequence
<220> FEATURE:
<223> OTHER INFORMATION: Synthetic peptide

<400> SEQUENCE: 119

Leu Ser Leu Asp Val Pro Thr Asn Ile Met Asn Leu Leu Phe Asn Ile
1               5                   10                  15

Ala Lys Ala Lys Asn Leu Arg Ala Gln Ala Ala Ala Asn Ala His Leu
            20                  25                  30

Met Ala Gln Ile
        35

<210> SEQ ID NO 120
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys, Tyr or Glu
<220> FEATURE:
<221> NAME/KEY: MOD_RES
<222> LOCATION: (37)..(37)
<223> OTHER INFORMATION: AMIDATION

<400> SEQUENCE: 120

Xaa Leu Ser Leu Asp Val Pro Thr Asn Ile Met Asn Leu Leu Phe Asn
1               5                   10                  15

Ile Ala Lys Ala Lys Asn Leu Arg Ala Gln Ala Ala Ala Asn Ala His
            20                  25                  30

Leu Met Ala Gln Ile
        35

-continued

```
<210> SEQ ID NO 121
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys, Tyr or Glu
<220> FEATURE:
<221> NAME/KEY: MOD_RES
<222> LOCATION: (38)..(38)
<223> OTHER INFORMATION: AMIDATION

<400> SEQUENCE: 121

Xaa Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 122
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys, Tyr or Glu
<220> FEATURE:
<221> NAME/KEY: MOD_RES
<222> LOCATION: (39)..(39)
<223> OTHER INFORMATION: AMIDATION

<400> SEQUENCE: 122

Xaa Phe Thr Leu Ser Leu Asp Val Pro Thr Asn Ile Met Asn Leu Leu
1               5                   10                  15

Phe Asn Ile Ala Lys Ala Lys Asn Leu Arg Ala Gln Ala Ala Ala Asn
            20                  25                  30

Ala His Leu Met Ala Gln Ile
        35

<210> SEQ ID NO 123
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Cys, Tyr or Glu
<220> FEATURE:
<221> NAME/KEY: MOD_RES
<222> LOCATION: (40)..(40)
<223> OTHER INFORMATION: AMIDATION

<400> SEQUENCE: 123

Xaa Lys Phe Thr Leu Ser Leu Asp Val Pro Thr Asn Ile Met Asn Leu
1               5                   10                  15
```

```
Leu Phe Asn Ile Ala Lys Ala Lys Asn Leu Arg Ala Gln Ala Ala Ala
                20              25                  30

Asn Ala His Leu Met Ala Gln Ile
        35              40
```

CRHR2 PEPTIDE AGONISTS AND USES THEREOF

CROSS REFERENCE TO RELATED APPLICATIONS

This application claims the benefit of U.S. provisional patent application Ser. Nos. 61/111,233, filed Nov. 4, 2008 and 61/178,890, filed May 15, 2009, which are hereby incorporated by reference

REFERENCE TO A SEQUENCE LISTING

Sequence Listing provided in text file submitted to the USPTO on May 25, 2012, said text file entitled PRD3040USNP_ST25.txt, created on May 25, 2012, and being 68 KB in size, the contents of which are hereby incorporated by reference.

FIELD OF THE INVENTION

The present invention generally relates to a peptide useful as a stresscopin mimetic for treating medical indications mediated by corticotrophin releasing hormone receptor 2 activity, constructs for peptide delivery, pharmaceutical compositions comprising them, and methods of treating a subject diagnosed with a disease, disorder, or medical condition mediated by corticotrophin releasing hormone receptor 2.

BACKGROUND

Heart failure is a common cardiovascular condition and has reached epidemic proportions in the United States and Europe (Remme et al., *Eur. Heart J.*, 2001, vol. 22, pp. 1527-1560). The number of hospital admissions for acute heart failure is approaching 1 million each year in the United States alone. Currently, readmission rates and mortality have reached 30% to 40% within 60 days following discharge (Cuffee et al., *JAMA*, 2002, vol. 287(12), pp. 1541-7). In acute heart failure, worsening of hemodynamic function, in particular with very high left ventricular end-diastolic pressure is common.

The current treatment for acute heart failure is multifactorial and often differs among patients. While diuretics, vasodilators, and positive inotropes remain the mainstay in the treatment of patients with acute heart failure, these treatments are associated with mortality and high readmission rates.

Furthermore, existing inotropic therapies (eg, dobutamine) result in improved cardiac output, but with increased heart rate and increased myocardial oxygen consumption. These inotropic agents also carry with them a proarrhythmic potential in patients with heart failure. This cardiac liability is believed to be associated with the energy expense and calcium drive associated with these agents' direct positive inotropic actions.

In an effort to meet this growing unmet medical need, many new approaches have been studied with limited success in safely improving the hemodynamic status and outcome of patients with this syndrome. One such agent, the peptide human urocortin 2 (h-UCN2), has been studied in healthy subjects and patients with heart failure. This peptide was shown to increase left ventricular ejection fraction (LVEF) and cardiac output (CO) in a model of heart failure in sheep (Rademaker et al., *Circulation*, 2005, vol. 112, pp. 3624-3624). In subsequent intravenous infusion studies in 8 healthy subjects (Davis et al., *J. Am. Coll. Cardiol.*, 2007, vol. 49, pp. 461-471) and in 8 subjects with heart failure (Davis et al., *Eur. Heart J.*, 2007, vol. 28, pp. 2589-2597), the increases in LVEF and CO were accompanied by an increase in heart rate and decrease in blood pressure at both doses examined in each of the two studies. One-hour intravenous infusions of h-UCN2 in healthy subjects and patients appears to have been well tolerated.

Human stresscopin (h-SCP), a 40-amino-acid peptide, is related to h-UCN2 and both are members of the corticotrophin releasing hormone (CRH) peptide family. The biological actions of the CRH peptide family are elicited by two 7 transmembrane G-protein coupled receptors, CRH receptor type 1 (CRHR1) and CRH receptor type 2 (CRHR2). Although these receptors contain high sequence homology, the different members of the CRH peptide family express significant differences in their relative binding affinity, degree of receptor activation and selectivity for these two receptors.

Unlike many of the CRH family members, h-SCP expresses greater selectivity for the CRHR2 and acts as a mediator that aids in the process of attenuating the initiation and maintenance of physiological stress (Bale et al., *Nat. Genet.*, 2000, vol. 24, pp. 410-414; Kishimoto et al., *Nat. Genet.*, 2000, vol. 24, pp. 415-419). In addition to its apparent role in physiological stress, h-SCP has been reported to elicit a number of other physiological actions. It exerts effects on the endocrine (Li et al., *Endocrinology*, 2003, vol. 144, pp. 3216-3224), central nervous, cardiovascular (Bale et al., *Proc. Natl. Acad. Sci.*, 2004, vol. 101, pp. 3697-3702; Tang et al., *Eur. Heart J.*, 2007, vol. 28, pp. 2561-2562), pulmonary, gastrointestinal, renal, skeletal muscle, and inflammatory systems (Moffatt et al., *FASEB J.*, 2006, vol. 20, pp. 1877-1879).

In addition, CRHR2 activity has been implicated in skeletal muscle wasting disease, such as sarcopenia (Hinkle et al., *Endocrinology*, 2003, vol. 144(11), pp. 4939-4946), motor activity and food intake (Ohata et al., *Peptides*, 2004, vol. 25, pp. 1703-1709), participates in a cardioprotective role (Brar et al., *Endocrinology*, 2004, vol. 145(1), pp. 24-35) and expresses bronchorelaxant and anti-inflammatory activity (Moffatt et al., *FASEB J.*, 2006, vol. 20, pp. E1181-E1187).

Pegylation is a process of attaching one or more polyethylene glycol (PEG) polymers to molecules. Often, the process of pegylation is applied to antibodies, peptides and proteins to improve their biopharmaceutical properties and overcome a compound's susceptibility to proteolytic enzymes, short circulation half-life, short shelf live, low solubility, rapid renal clearance and the potential to generate antibodies to the administered drug (Harris et al., *Nature*, 2003, vol. 2, pp. 214-221; Hamidi et al., *Drug Delivery*, 2006, 3, pp. 399-409; Bailon et al., *PSTT*, 1998, vol. 1(8), pp. 352356). Recently, the FDA has approved PEG polymers for use as a vehicle or base in foods, cosmetics, and pharmaceuticals. Overall, PEG polymers are relatively non-immunogenic, have little toxicity, and are eliminated intact by the kidneys or in the feces. These features can result in a number of clinical benefits for the compound if this process is developed to preserve or improve the affinity, efficacy and pharmacologic profile of the parent molecule.

SUMMARY

The invention is directed to the general and preferred embodiments defined, respectively, by the independent and dependent claims appended hereto, which are incorporated by reference herein. Preferred and exemplary features of the invention will be apparent from the detailed description below with reference to the drawing figures.

In certain embodiments, the invention relates to a peptide having agonist activity towards corticotrophin releasing hormone receptor type 2 (CRHR2) comprising the amino acid sequence of

```
                                     (SEQ ID NO: 119)
LSLDV PTNIM NLLFN IAKAK NLRAQ AAANA HLMAQ I,
``` wherein at least one amino acid of the peptide is substituted with X provided that the substitution is not made at positions 3, 29, and 33 of the amino acid sequence, and wherein X is cysteine, tyrosine, or glutamic acid; or a pharmaceutically acceptable salt or amide thereof.

The CRHR2 peptide agonists embodied in this invention comprise amino acid sequences that are relatively similar to the sequences of human Stresscopin and human Urocortin III.

In one embodiment, an amino acid substitution to the above referenced amino acid sequence is selected from the group consisting of: X for L at position 1; X for S at position 2; X for D at position 4; X for V at position 5; X for P at position 6; X for T at position 7; X for N at position 8; X for I at position 9; X for M at position 10; X for N at position 11; X for L at position 12; X for L at position 13; X for F at position 14; X for N at position 15; X for I at position 16; X for A at position 17; X for K at position 18; X for A at position 19; X for K at position 20; X for N at position 21; X for L at position 22; X for R at position 23; X for A at position 24; X for Q at position 25; X for A at position 26; X for A at position 27; X for A at position 28; X for A at position 30; X for H at position 31; X for L at position 32; X for A at position 34; X for Q at position 35; and X for I at position 36.

The invention also relates to a pharmaceutically acceptable salt or an amide of the CRHR2 peptide agonists and is furthermore directed to a pharmaceutical composition of said peptides in combination with one or more pharmaceutically acceptable excipients.

In yet another embodiment, the amino acid sequence of the CRHR2 peptide agonist is selected from the group consisting of:

```
                                     (SEQ ID NO: 120)
XLSLD VPTNI MNLLF NIAKA KNLRA QAAAN AHLMA QI-NH₂;

(SEQ ID NO: 121)
XTLSL DVPTN IMNLL FNIAK AKNLR AQAAA NAHLM AQI-NH₂;

(SEQ ID NO: 122)
XFTLS LDVPT NIMNL LFNIA KAKNL RAQAA ANAHL MAQI-
NH₂;
and
                                     (SEQ ID NO: 123)
XKFTL SLDVP TNIMN LLFNI AKAKN LRAQA AANAH LMAQI-
NH₂.
```

In another embodiment, a conjugate comprises the amino acid sequence and a linker attached to the X of the CRHR2 peptide agonist. Preferably, the X is cysteine. Preferably, the linker is acetamide or N-ethylsuccinimide.

In yet another embodiment, a conjugate of the agonist peptide comprises polyethylene glycole (PEG) attached to the linker that possess a molecular weight of not more than 80 kDa. Preferably, the PEG has a molecular weight of either about 2 kDa, about 5 kDa, about 12 kDa, about 20 kDa, about 30 kDa or about 40 kDa.

A linker allows for more easily and selectively attaching the PEG with regard to the position in the amino acid sequence to the peptide, while pegylation of the peptide prolongs the half-life of the pegylated peptide, thereby extending the duration of therapeutic benefit to a patient. Therefore, the substitution to the amino acid sequence of the CRHR2 peptide agonist is preferably such that there is at least one amino acid of type X in the sequence. This will ensure that pegylation of the peptide is directed at least one position in the sequence.

In certain embodiments, the CRHR2 peptide agonist comprises one of the following amino acid sequences contained in SEQ ID NO.s 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 35, 36, 37, 39, 40, and 41.

Another aspect of the invention is directed to method of treating a subject suffering from or diagnosed with a disease, disorder, or medical condition mediated by corticotrophin releasing hormone receptor type 2 activity that is either a metabolic disease or heart failure. The method comprises the administration to a subject in need of such treatment an effective amount of a CRHR2 peptide agonist embodied in this invention.

Additional embodiments and advantages of the invention will become apparent from the detailed discussion, schemes, examples, and claims below.

BRIEF DESCRIPTION OF THE FIGURES

FIG. 6 shows the relaxation of precontracted, isolated rat aorta by peptide agonists with SEQ ID NO:1 and SEQ ID NO:115 (h-UCN2).

FIG. 7 illustrates the heart rate, left ventricular developed pressure, and coronary perfusion pressure changes in Langendorff perfused rabbit hearts in the presence of peptide agonist with SEQ ID NO:1 and placebo control vehicle.

DETAILED DESCRIPTION OF THE INVENTION

Figure 1A:
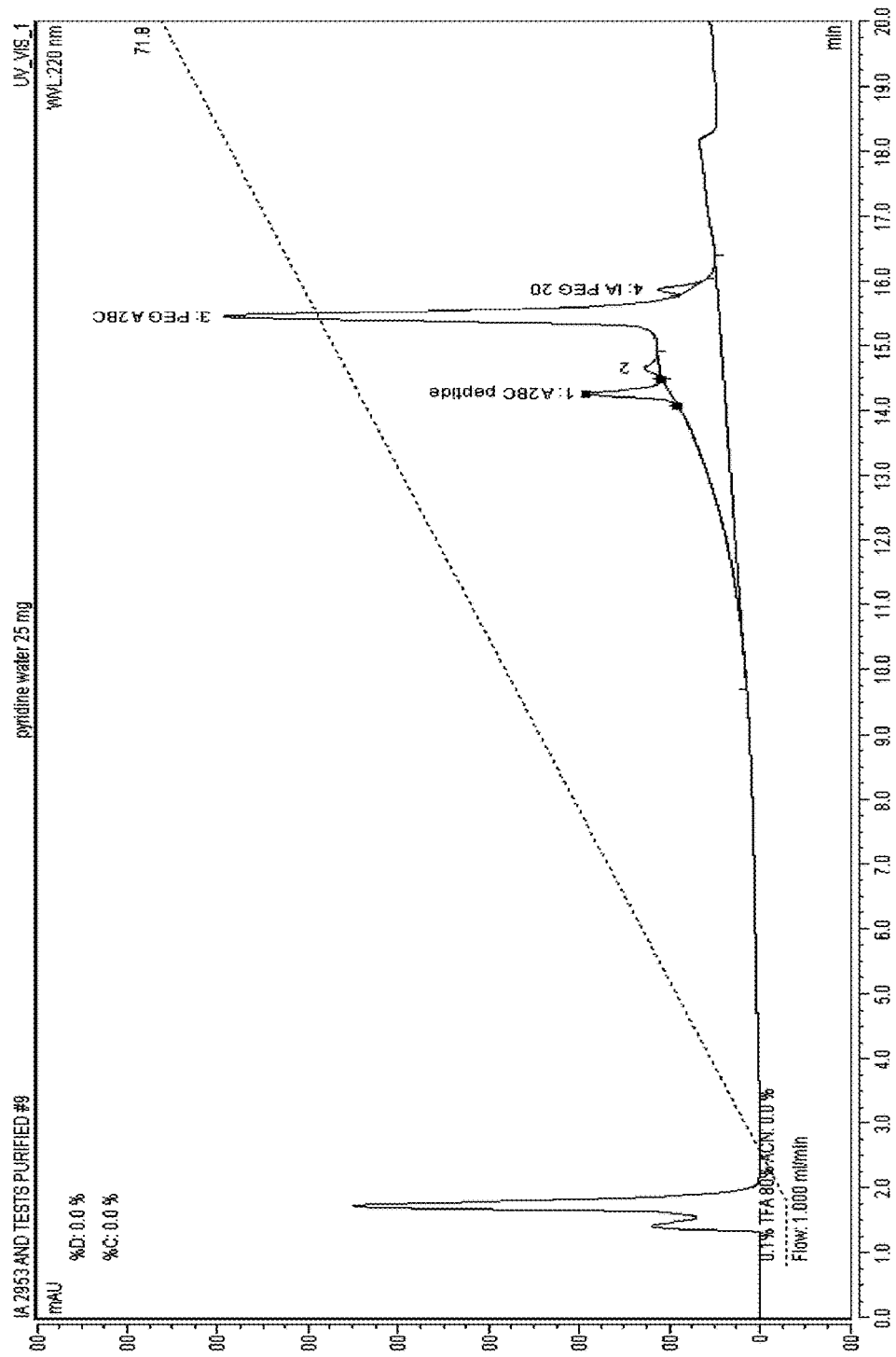
FIGS. 1A & B show the analytical HPLC trace of a peptide agonist with SEQ ID NO:102 derivatized with iodoacetamide-PEG after 2 hours reaction time and after purification, respectively.

This invention relates to novel peptides that are CHRH2 peptide agonists and compositions thereof for the treatment, amelioration or inhibition of cardiovascular conditions, including but not limited to heart failure, as well as metabolic diseases.

In one embodiment of the invention, a method of treating or ameliorating heart failure in a subject in need thereof comprises administering to the subject a therapeutically effective amount of at least one CRHR2 peptide agonist.

In certain embodiments, the CRHR2 peptide is a mammalian peptide, specifically, a mouse, rat, guinea pig, rabbit, dog, cat, horse, cow, pig, or primate peptide, or modifications thereof. Preferably, the peptide is a modified human peptide. Examples of the inventive CRHR2 peptide agonists are described in more detail in the section below.

Another embodiment of the invention comprises a reactive group covalently attached to a peptide agonist. The reactive group is chosen for its ability to form a stable covalent bond with a polymer or other chemical moiety that extends the circulation half-life of the peptide in the subject. In an embodiment, such a polymer comprises a polyethylene glycol (PEG) polymer that prolongs the duration of the peptide in the subject's circulation before its elimination. In this form the reactive group is acting as linker between the peptide by reacting on one hand with one or more amino acids of the peptide and on the other with the polymer. In an alternative embodiment, the reactive group is initially bound to the PEG before forming a chemical bond with peptide. In a preferred embodiment of the modified peptides, the linker group is a succinimide, more particular an N-ethylsuccinimide, or an acetamide. Furthermore, the linker may be vinyl sulphone or orthopyridyl disulfide. Preferably, chemical modifications are performed on isolated peptides, e.g. to increase the reaction efficiencies.

Linkers that are useful to bind the peptide and the PEG moiety would convey minimal immunogenicity and toxicity to the host. Examples of such linkers may be found in Bailon et al., *PSTT,* 1998, vol. 1(8), pp. 352-356 or Roberts et al., 2002, *Adv. Drug Del. Rev., vol.* 54, pp. 459-476. Examples of suitable chemical moieties, in particular PEGs and equivalent polymers, are described in Greenwald et al., 2003, *Adv. Drug Del. Rev., vol.* 55, pp. 217-250. For example, styrene-maleic anhydride neocarzinostatin copolymer, hydroxylpropyl methacrylamide copolymer, dextran, polyglutamic acid, hydroxylethyl starch, and polyaspartic acid are other polymeric systems that can be employed to accomplish delivery and pharmacokinetic characteristics similar to a PEG system.

In certain embodiments of the invention, the CRHR2 peptide agonist contains an amidated C-terminus. Such modification procedures may be performed on an isolated purified peptide or, as in the case of solid-phase synthesis, may be performed during the synthesis procedure. Such procedures are reviewed in Ray et al., *Nature Biotech.,* 1993, vol. 11, pp. 64-70; Cottingham et al., *Nature Biotech.,* 2001, vol. 19, pp. 974-977; Walsh et al., *Nature Biotech.,* vol. 24, pp. 1241-1252; and U.S. Pat. Pub. No. 2008/0167231.

In a particular embodiment of the invention, the compound comprises the peptide of an amino acid sequence as set forth in SEQ ID NO:82 or in SEQ ID NO:102 containing a CONH2 at its carboxy terminus and a linker bound to the cysteine residue at position 28 of the amino acid sequence with the linker being N-ethylsuccinimide or acetamide, and the linker attached to a PEG polymer of about 20 kDa.

Furthermore, one embodiment of the present invention also features a method of treating a subject suffering or diagnosed with a disease, disorder or condition mediated by CHRH2 activity comprising administering to the subject a therapeutically effective amount of at least one CRHR2 peptide agonist.

Another embodiment of the present invention also features a method for treating or inhibiting the progression of one or more CHRH2-mediated conditions, diseases, or disorders, said method comprising administering to a patient in need of treatment a pharmaceutically effective amount of at least one CRHR2 peptide agonist.

It is a further embodiment of the invention to provide a process of making a pharmaceutical composition comprising admixing any of the CRHR2 peptide agonists and a pharmaceutically acceptable carrier.

Terms and Definitions

The present invention is best understood by reference to the following definitions, the drawings and exemplary disclosure provided herein.

The following are abbreviations that are at times used in this specification: $pA_{50}$ or $pEC_{50}$=negative logarithm base 10 of the agonist concentration required to produce half maximum effect; SEM=standard error of the mean; Log DR=logarithm base 10 of the agonist dose ratio; MW=molecular weight; cAMP=adenosine 3',5'-cyclic monophosphate; cDNA=complementary DNA; kb=kilobase (1000 base pairs); kDa=kilodalton; ATP=adenosine 5'-triphosphate; nt=nucleotide; bp=base pair; PAGE=polyacrylamide gel electrophoresis; PCR=polymerase chain reaction, nm=nanomolar.

The terms "comprising", "containing", and "including," are used herein in their open, non-limiting sense.

"Administering" or "administration" means providing a drug to a patient in a manner that is pharmacologically useful.

"Composition" means a product containing a compound of the present invention (such as a product comprising the specified ingredients in the specified amounts, as well as any product which results, directly or indirectly, from such combinations of the specified ingredients in the specified amounts).

"Compound" or "drug" means CRHR2 peptide agonist or pharmaceutically acceptable forms thereof. "Conjugate" means a chemical compound that has been formed by the joining of two or more compounds.

"Dosage form" means one or more compounds in a medium, carrier, vehicle, or device suitable for administration to a patient. "Oral dosage form" means a dosage form suitable for oral administration.

"Dose" means a unit of drug. Conventionally, a dose is provided as a dosage form. Doses may be administered to patients according to a variety of dosing regimens. Common dosing regimens include once daily orally (qd), twice daily orally (bid), and thrice daily orally (tid).

"Forms" means various isomers and mixtures of one or more CRHR2 peptide agonists. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers). The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry.

"Medicament" means a product for use in preventing, treating or ameliorating substance related disorders such as substance dependence, substance abuse or substance induced disorders in a subject in need thereof.

"Patient" or "subject" means an animal, preferably a mammal, more preferably a human, in need of therapeutic intervention.

"Pharmaceutically acceptable" means molecular entities and compositions that are of sufficient purity and quality for use in the formulation of a composition or medicament of the present invention. Since both human use (clinical and over-the-counter) and veterinary use are equally included within the scope of the present invention, a formulation would include a composition or medicament for either human or veterinary use.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Pharmaceutically acceptable salt" means an acid or base salt of the compounds of the invention that is of sufficient purity and quality for use in the formulation of a composition or medicament of the present invention and are tolerated and sufficiently non-toxic to be used in a pharmaceutical preparation. Suitable pharmaceutically acceptable salts include acid addition salts which may, for example, be formed by reacting the drug compound with a suitable pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

"CRHR2 peptide agonist" means a peptide or derivative thereof that exhibits agonist activity towards corticotrophin releasing hormone receptor type 2 (CRHR2). Preferably a CRHR2 peptide agonist is a stresscopin derivative or variant that can also exhibit activity towards corticotrophin releasing hormone receptor type 1 (CRHR1). A CRHR2 peptide agonist generally is a selective CRHR2 agonist with less activity towards CRHR1. Selectivity towards a receptor hereby refers to the potency of a peptide to induce an activity response in the receptor that the peptide is selective towards in comparison to other receptors, in which the peptide might also induce activity, but with less potency. The definition of a CRHR2 peptide agonist is not limited to agonist, but can also include partial agonists. The CRHR1 and CRHR2 activity of a CRHR2 peptide agonist can for instance be assessed in an adenosine 3',5'-cyclic monophosphate (cAMP) assay.

closely resemble the CRHR2 activity of stresscopin (h-SCP),

"Therapeutically effective amount" means that amount of compound that elicits the biological or medicinal response in a tissue system, animal or human, that is being sought by a researcher, veterinarian, medical doctor, or other clinician, which includes therapeutic alleviation of the symptoms of the disease or disorder being treated and prophylactic.

The term "treating" as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating.

Compounds

The present invention relates to the following peptides and modifications thereof. Compounds of the present invention also include novel and selective CRHR2 agonist peptides and modifications thereof.

Furthermore, compounds of the present invention refer to peptidic moieties that bind to or complex with CRHR2, such as h-SCP or mimetic h-SCP peptides. Preferred compounds are peptides that have agonistic activity towards CRHR2 as for example measured in a cAMP assay with a $pA_{50}$ that is within the range of about 7.5 and higher, or $pK_I$ (negative logarithm of $K_I$) measured in a radioligand binding assay that is within the range of about 7.5 and higher. Besides displaying binding affinity CRHR2 peptide agonists should demonstrate some level of receptor activation. Peptides that are homologous to h-SCP are therefore preferable, since these peptides naturally possess similar physical and chemical properties.

Members of the family of corticotropin releasing factors exhibit a moderately short half-life. CRHR2 peptide agonists promise a unique therapeutic profile. For the treatment of disorders that are mediated by CRHR2, including but not limited to, cardiovascular and metabolic disease, one embodiment of this invention is directed to a long acting form of peptide agonists. A long acting CRHR2 peptide agonist provides particular benefits for the treatment of chronic disorders where the need for continued therapeutic exposure and patient compliance with prescribed treatment are a challenge.

Accordingly, one embodiment of the current invention is directed in general to sequence variation(s) of h-SCP, site specific sequence variations, and spatial or steric interference considerations such that the desired therapeutic profile and/or structure-activity relationship relative to CRHR2 is retained.

Examples of CRHR2 peptide agonists, which are optionally amidated at the C-termini, are provided in Tables 1 through 5. The reactive group or linker is preferably succinimide or acetamide. The modified peptides optionally contain a PEG group. The PEG varies in length and weight, and is preferably about 20 kDa. Optionally, the number of reactive groups can be more than one, with one reactive group being preferable.

TABLE 1

Human stresscopin with amidated C-terminus and Cys-variant CRHR2 peptide agonists

| | | | | | | | | |
|---|---|---|---|---|---|---|---|---|
| TKFTL | SLDVP | TNIMN | LLFNI | AKAKN | LRAQA | AANAH | LMAQI-NH$_2$ | SEQ ID NO: 1 |
| CKFTL | SLDVP | TNIMN | LLFNI | AKAKN | LRAQA | AANAH | LMAQI-NH$_2$ | SEQ ID NO: 2 |
| TCFTL | SLDVP | TNIMN | LLFNI | AKAKN | LRAQA | AANAH | LMAQI-NH$_2$ | SEQ ID NO: 3 |

TABLE 1-continued

Human stresscopin with amidated C-terminus and Cys-variant CRHR2 peptide agonists

| | |
|---|---|
| TKCTL SLDVP TNIMN LLFNI AKAKN LRAQA AANAH LMAQI-NH$_2$ | SEQ ID NO: 4 |
| TKFCL SLDVP TNIMN LLFNI AKAKN LRAQA AANAH LMAQI-NH$_2$ | SEQ ID NO: 5 |
| TKFTC SLDVP TNIMN LLFNI AKAKN LRAQA AANAH LMAQI-NH$_2$ | SEQ ID NO: 6 |
| TKFTL CLDVP TNIMN LLFNI AKAKN LRAQA AANAH LMAQI-NH$_2$ | SEQ ID NO: 7 |
| TKFTL SCDVP TNIMN LLFNI AKAKN LRAQA AANAH LMAQI-NH$_2$ | SEQ ID NO: 8 |
| TKFTL SLCVP TNIMN LLFNI AKAKN LRAQA AANAH LMAQI-NH$_2$ | SEQ ID NO: 9 |
| TKFTL SLDCP TNIMN LLFNI AKAKN LRAQA AANAH LMAQI-NH$_2$ | SEQ ID NO: 10 |
| TKFTL SLDVC TNIMN LLFNI AKAKN LRAQA AANAH LMAQI-NH$_2$ | SEQ ID NO: 11 |
| TKFTL SLDVP CNIMN LLFNI AKAKN LRAQA AANAH LMAQI-NH$_2$ | SEQ ID NO: 12 |
| TKFTL SLDVP TCIMN LLFNI AKAKN LRAQA AANAH LMAQI-NH$_2$ | SEQ ID NO: 13 |
| TKFTL SLDVP TNCMN LLFNI AKAKN LRAQA AANAH LMAQI-NH$_2$ | SEQ ID NO: 14 |
| TKFTL SLDVP TNICN LLFNI AKAKN LRAQA AANAH LMAQI-NH$_2$ | SEQ ID NO: 15 |
| TKFTL SLDVP TNIMC LLFNI AKAKN LRAQA AANAH LMAQI-NH$_2$ | SEQ ID NO: 16 |
| TKFTL SLDVP TNIMN CLFNI AKAKN LRAQA AANAH LMAQI-NH$_2$ | SEQ ID NO: 17 |
| TKFTL SLDVP TNIMN LCFNI AKAKN LRAQA AANAH LMAQI-NH$_2$ | SEQ ID NO: 18 |
| TKFTL SLDVP TNIMN LLCNI AKAKN LRAQA AANAH LMAQI-NH$_2$ | SEQ ID NO: 19 |
| TKFTL SLDVP TNIMN LLFCI AKAKN LRAQA AANAH LMAQI-NH$_2$ | SEQ ID NO: 20 |
| TKFTL SLDVP TNIMN LLFNC AKAKN LRAQA AANAH LMAQI-NH$_2$ | SEQ ID NO: 21 |
| TKFTL SLDVP TNIMN LLFNI CKAKN LRAQA AANAH LMAQI-NH$_2$ | SEQ ID NO: 22 |
| TKFTL SLDVP TNIMN LLFNI ACAKN LRAQA AANAH LMAQI-NH$_2$ | SEQ ID NO: 23 |
| TKFTL SLDVP TNIMN LLFNI AKCKN LRAQA AANAH LMAQI-NH$_2$ | SEQ ID NO: 24 |
| TKFTL SLDVP TNIMN LLFNI AKACN LRAQA AANAH LMAQI-NH$_2$ | SEQ ID NO: 25 |
| TKFTL SLDVP TNIMN LLFNI AKAKC LRAQA AANAH LMAQI-NH$_2$ | SEQ ID NO: 26 |
| TKFTL SLDVP TNIMN LLFNI AKAKN CRAQA AANAH LMAQI-NH$_2$ | SEQ ID NO: 27 |
| TKFTL SLDVP TNIMN LLFNI AKAKN LCAQA AANAH LMAQI-NH$_2$ | SEQ ID NO: 28 |
| TKFTL SLDVP TNIMN LLFNI AKAKN LRCQA AANAH LMAQI-NH$_2$ | SEQ ID NO: 29 |
| TKFTL SLDVP TNIMN LLFNI AKAKN LRACA AANAH LMAQI-NH$_2$ | SEQ ID NO: 30 |
| TKFTL SLDVP TNIMN LLFNI AKAKN LRAQC AANAH LMAQI-NH$_2$ | SEQ ID NO: 31 |
| TKFTL SLDVP TNIMN LLFNI AKAKN LRAQA CANAH LMAQI-NH$_2$ | SEQ ID NO: 32 |
| TKFTL SLDVP TNIMN LLFNI AKAKN LRAQA ACNAH LMAQI-NH$_2$ | SEQ ID NO: 33 |
| TKFTL SLDVP TNIMN LLFNI AKAKN LRAQA AACAH LMAQI-NH$_2$ | SEQ ID NO: 34 |
| TKFTL SLDVP TNIMN LLFNI AKAKN LRAQA AANCH LMAQI-NH$_2$ | SEQ ID NO: 35 |
| TKFTL SLDVP TNIMN LLFNI AKAKN LRAQA AANAC LMAQI-NH$_2$ | SEQ ID NO: 36 |
| TKFTL SLDVP TNIMN LLFNI AKAKN LRAQA AANAH CMAQI-NH$_2$ | SEQ ID NO: 37 |
| TKFTL SLDVP TNIMN LLFNI AKAKN LRAQA AANAH LCAQI-NH$_2$ | SEQ ID NO: 38 |
| TKFTL SLDVP TNIMN LLFNI AKAKN LRAQA AANAH LMCQI-NH$_2$ | SEQ ID NO: 39 |
| TKFTL SLDVP TNIMN LLFNI AKAKN LRAQA AANAH LMACI-NH$_2$ | SEQ ID NO: 40 |
| TKFTL SLDVP TNIMN LLFNI AKAKN LRAQA AANAH LMAQC-NH$_2$ | SEQ ID NO: 41 |

TABLE 2

Cys-variant of stresscopin peptide with
N-Ethylsuccinimide (NES) reactive group

| | |
|---|---|
| TKFTL SLDVP TNIMN LLFNI AKAKN LRAQA AANAH LMAQC(-NES)-NH₂ | SEQ ID NO: 42 |
| TKFTL SLDVP TNIMN LLFNI AKAKN LRAQA AANAC(-NES) LMAQI-NH₂ | SEQ ID NO: 43 |
| TKFTL SLDVP TNIMN LLFNI AKAKN LRAQA AAC(-NES)AH LMAQI-NH₂ | SEQ ID NO: 44 |
| TKFTL SLDVP TNIMN LLFNI AKAKN LRAQA AC(-NES)NAH LMAQI-NH₂ | SEQ ID NO: 45 |
| TKFTL SLDVP TNIMN LLFNI AKAKN LRAQA C(-NES)ANAH LMAQI-NH₂ | SEQ ID NO: 46 |
| TKFTL SLDVP TNIMN LLFNI AKAKN LRC(-NES)QA AANAH LMAQI-NH₂ | SEQ ID NO: 47 |
| TKFTL SLDVP TNIMN LLFNI AKAKN C(-NES)RAQA AANAH LMAQI-NH₂ | SEQ ID NO: 48 |
| TKFTL SLDVP TNIMN LLFNI AKAKC(-NES) LRAQA AANAH LMAQI-NH₂ | SEQ ID NO: 49 |
| TKFTL SLDVP TNIMN LLFNI AKAC(-NES)N LRAQA AANAH LMAQI-NH₂ | SEQ ID NO: 50 |
| TKFTL SLDVP TNIMN LLFNC(-NES) AKAKN LRAQA AANAH LMAQI-NH₂ | SEQ ID NO: 51 |
| TKFTL SLDVP TNIMN LLFC(-NES)I AKAKN LRAQA AANAH LMAQI-NH₂ | SEQ ID NO: 52 |
| TKFTL SLDVP TNIMN LC(-NES)FNI AKAKN LRAQA AANAH LMAQI-NH₂ | SEQ ID NO: 53 |
| TKFTL SLDVP TNIMN C(-NES)LFNI AKAKN LRAQA AANAH LMAQI-NH₂ | SEQ ID NO: 54 |

TABLE 3

Pegylated Cys-variant CRHR2 peptide agonists with
N-Ethylsuccinimide (NES) linker and PEG weighing about 20 kDa

| | |
|---|---|
| C(-NES-PEG)KFTL SLDVP TNIMN LLFNI AKAKN LRAQA AANAH LMAQI-NH₂ | SEQ ID NO: 55 |
| TC(-NES-PEG)FTL SLDVP TNIMN LLFNI AKAKN LRAQA AANAH LMAQI-NH₂ | SEQ ID NO: 56 |
| TKC(-NES-PEG)TL SLDVP TNIMN LLFNI AKAKN LRAQA AANAH LMAQI-NH₂ | SEQ ID NO: 57 |
| TKFC(-NES-PEG)L SLDVP TNIMN LLFNI AKAKN LRAQA AANAH LMAQI-NH₂ | SEQ ID NO: 58 |
| TKFTC(-NES-PEG) SLDVP TNIMN LLFNI AKAKN LRAQA AANAH LMAQI-NH₂ | SEQ ID NO: 59 |
| TKFTL C(-NES-PEG)LDVP TNIMN LLFNI AKAKN LRAQA AANAH LMAQI-NH₂ | SEQ ID NO: 60 |
| TKFTL SC(-NES-PEG)DVP TNIMN LLFNI AKAKN LRAQA AANAH LMAQI-NH₂ | SEQ ID NO: 61 |
| TKFTL SLC(-NES-PEG)VP TNIMN LLFNI AKAKN LRAQA AANAH LMAQI-NH₂ | SEQ ID NO: 62 |
| TKFTL SLDC(-NES-PEG)P TNIMN LLFNI AKAKN LRAQA AANAH LMAQI-NH₂ | SEQ ID NO: 63 |
| TKFTL SLDVC(-NES-PEG) TNIMN LLFNI AKAKN LRAQA AANAH LMAQI-NH₂ | SEQ ID NO: 64 |
| TKFTL SLDVP C(-NES-PEG)NIMN LLFNI AKAKN LRAQA AANAH LMAQI-NH₂ | SEQ ID NO: 65 |
| TKFTL SLDVP TC(-NES-PEG)IMN LLFNI AKAKN LRAQA AANAH LMAQI-NH₂ | SEQ ID NO: 66 |
| TKFTL SLDVP TNC(-NES-PEG)MN LLFNI AKAKN LRAQA AANAH LMAQI-NH₂ | SEQ ID NO: 67 |
| TKFTL SLDVP TNIC(-NES-PEG)N LLFNI AKAKN LRAQA AANAH LMAQI-NH₂ | SEQ ID NO: 68 |
| TKFTL SLDVP TNIMC(-NES-PEG) LLFNI AKAKN LRAQA AANAH LMAQI-NH₂ | SEQ ID NO: 69 |
| TKFTL SLDVP TNIMN C(-NES-PEG)LFNI AKAKN LRAQA AANAH LMAQI-NH₂ | SEQ ID NO: 70 |
| TKFTL SLDVP TNIMN LC(-NES-PEG)FNI AKAKN LRAQA AANAH LMAQI-NH₂ | SEQ ID NO: 71 |
| TKFTL SLDVP TNIMN LLC(-NES-PEG)NI AKAKN LRAQA AANAH LMAQI-NH₂ | SEQ ID NO: 72 |
| TKFTL SLDVP TNIMN LLFC(-NES-PEG)I AKAKN LRAQA AANAH LMAQI-NH₂ | SEQ ID NO: 73 |
| TKFTL SLDVP TNIMN LLFNC(-NES-PEG) AKAKN LRAQA AANAH LMAQI-NH₂ | SEQ ID NO: 74 |
| TKFTL SLDVP TNIMN LLFNI C(-NES-PEG)KAKN LRAQA AANAH LMAQI-NH₂ | SEQ ID NO: 75 |
| TKFTL SLDVP TNIMN LLFNI AC(-NES-PEG)AKN LRAQA AANAH LMAQI-NH₂ | SEQ ID NO: 76 |

TABLE 3-continued

Pegylated Cys-variant CRHR2 peptide agonists with
N-Ethylsuccinimide (NES) linker and PEG weighing about 20 kDa

| | |
|---|---|
| TKFTL SLDVP TNIMN LLFNI AKC(-NES-PEG)KN LRAQA AANAH LMAQI-NH$_2$ | SEQ ID NO: 77 |
| TKFTL SLDVP TNIMN LLFNI AKAC(-NES-PEG)N LRAQA AANAH LMAQI-NH$_2$ | SEQ ID NO: 78 |
| TKFTL SLDVP TNIMN LLFNI AKAKC(-NES-PEG) LRAQA AANAH LMAQI-NH$_2$ | SEQ ID NO: 79 |
| TKFTL SLDVP TNIMN LLFNI AKAKN C(-NES-PEG)RAQA AANAH LMAQI-NH$_2$ | SEQ ID NO: 80 |
| TKFTL SLDVP TNIMN LLFNI AKAKN LC(-NES-PEG)AQA AANAH LMAQI-NH$_2$ | SEQ ID NO: 81 |
| TKFTL SLDVP TNIMN LLFNI AKAKN LRC(-NES-PEG)QA AANAH LMAQI-NH$_2$ | SEQ ID NO: 82 |
| TKFTL SLDVP TNIMN LLFNI AKAKN LRAC(-NES-PEG)A AANAH LMAQI-NH$_2$ | SEQ ID NO: 83 |
| TKFTL SLDVP TNIMN LLFNI AKAKN LRAQC(-NES-PEG) AANAH LMAQI-NH$_2$ | SEQ ID NO: 84 |
| TKFTL SLDVP TNIMN LLFNI AKAKN LRAQA C(-NES-PEG)ANAH LMAQI-NH$_2$ | SEQ ID NO: 85 |
| TKFTL SLDVP TNIMN LLFNI AKAKN LRAQA AC(-NES-PEG)NAH LMAQI-NH$_2$ | SEQ ID NO: 86 |
| TKFTL SLDVP TNIMN LLFNI AKAKN LRAQA AAC(-NES-PEG)AH LMAQI-NH$_2$ | SEQ ID NO: 87 |
| TKFTL SLDVP TNIMN LLFNI AKAKN LRAQA AANC(-NES-PEG)H LMAQI-NH$_2$ | SEQ ID NO: 88 |
| TKFTL SLDVP TNIMN LLFNI AKAKN LRAQA AANAC(-NES-PEG) LMAQI-NH$_2$ | SEQ ID NO: 89 |
| TKFTL SLDVP TNIMN LLFNI AKAKN LRAQA AANAH C(-NES-PEG)MAQI-NH$_2$ | SEQ ID NO: 90 |
| TKFTL SLDVP TNIMN LLFNI AKAKN LRAQA AANAH LC(-NES-PEG)AQI-NH$_2$ | SEQ ID NO: 91 |
| TKFTL SLDVP TNIMN LLFNI AKAKN LRAQA AANAH LMC(-NES-PEG)QI-NH$_2$ | SEQ ID NO: 92 |
| TKFTL SLDVP TNIMN LLFNI AKAKN LRAQA AANAH LMAC(-NES-PEG)I-NH$_2$ | SEQ ID NO: 93 |
| TKFTL SLDVP TNIMN LLFNI AKAKN LRAQA AANAH LMAQC(-NES-PEG)-NH$_2$ | SEQ ID NO: 94 |

TABLE 4

Pegylated Cys-variant CRHR2 peptide agonists with PEGs of variable
molar weight and N-Ethylsuccinimide (NES) or Acetamide IA linker

| | |
|---|---|
| TKFTL SLDVP TNIMN LLFNI AKAKN LRC(-NES-PEG MW2000)QA AANAH LMAQI-NH$_2$ | SEQ ID NO: 95 |
| TKFTL SLDVP TNIMN LLFNI AKAKN LRC(-NES-PEG MW5000)QA AANAH LMAQI-NH$_2$ | SEQ ID NO: 96 |
| TKFTL SLDVP TNIMN LLFNI AKAKN LRC(-NES-PEG MW12000)QA AANAH LMAQI-NH$_2$ | SEQ ID NO: 97 |
| TKFTL SLDVP TNIMN LLFNI AKAKN LRC(-NES-PEG MW20000)QA AANAH LMAQI-NH$_2$ | SEQ ID NO: 82 |
| TKFTL SLDVP TNIMN LLFNI AKAKN LRC(-NES-PEG-NEM[a] MW20000)QA AANAH LMAQI-NH$_2$ | SEQ ID NO: 98 |
| TKFTL SLDVP TNIMN LLFNI AKAKN LRC(-NES-PEG MW30000)QA AANAH LMAQI-NH$_2$ | SEQ ID NO: 99 |
| TKFTL SLDVP TNIMN LLFNI AKAKN LRC(-NES-PEG MW40000)QA AANAH LMAQI-NH$_2$ | SEQ ID NO: 100 |
| TKFTL SLDVP TNIMN LLFNI AKAKN LRC(-NES-PEG MW80000 & BRANCHED)QA AANAH LMAQI-NH$_2$ | SEQ ID NO: 101 |
| TKFTL SLDVP TNIMN LLFNI AKAKN LRC(-IA-PEG MW20000)QA AANAH LMAQI-NH$_2$ | SEQ ID NO: 102 |
| TKFTL SLDVP TNIMN LLFNI AKAKN LRC(-IA-PEG MW30000)QA AANAH LMAQI-NH$_2$ | SEQ ID NO: 103 |

TABLE 4-continued

Pegylated Cys-variant CRHR2 peptide agonists with PEGs of variable molar weight and N-Ethylsuccinimide (NES) or Acetamide IA linker

| | |
|---|---|
| TKFTL SLDVP TNIMN LLFNI AKAKN LRC(-IA-PEG MW40000)QA AANAH LMAQI-NH$_2$ | SEQ ID NO: 104 |
| TKFTL SLDVP TC(-IA-PEG MW20000)IMN LLFNI AKAKN LRAQA AANAH LMAQI-NH$_2$ | SEQ ID NO: 105 |
| TKFTL SLDVP TNIMN LLFNI AKAKN LRAQA AANAC(-IA-PEG MW20000) LMAQI-NH$_2$ | SEQ ID NO: 106 |

$^a$NES-PEG-NEM double-ended linear PEG with an N-Ethylmaleimide cap at the non-linked end of the PEG chain.

TABLE 5

CRHR2 peptide agonists with shortened amino acid (aa) sequence compared to peptide of SEQ ID NO: 1

| | | |
|---|---|---|
| TKFTL SLDVP TNIMN LLFNI AKAKN LRAQA AANAH LMAQI-NH$_2$ | 40aa | SEQ ID NO: 1 |
| KFTLS LDVPT NIMNL LFNIA KAKNL RAQAA ANAHL MAQI-NH$_2$ | 39aa | SEQ ID NO: 107 |
| TLSLD VPTNI MNLLF NIAKA KNLRA QAAAN AHLMA QI-NH$_2$ | 37aa | SEQ ID NO: 108 |
| LSLDV PINIM NLLFN IAKAK NLRAQ AAANA HLMAQ I-NH$_2$ | 36aa | SEQ ID NO: 109 |
| SLDVP TNIMN LLFNI AKAKN LRAQA AANAH LMAQI-NH$_2$ | 35aa | SEQ ID NO: 110 |
| LDVPT NIMNL LFNIA KAKNL RAQAA ANAHL MAQI-NH$_2$ | 34aa | SEQ ID NO: 111 |
| DVPTN IMNLL FNIAK AKNLR AQAAA NAHLM AQI-NH$_2$ | 33aa | SEQ ID NO: 112 |
| FTLSL DVPTN IMNLL FNIAK AKNLR AQAAA NAHLM AQI-NH$_2$ | h-UCN3 | SEQ ID NO: 116 |

Drug compounds of the present invention also include a mixture of stereoisomers, or each pure or substantially pure isomer. For example, the present compound may optionally have one or more asymmetric centers at a carbon atom containing any one substituent. Therefore, the compound may exist in the form of enantiomer or diastereomer, or a mixture thereof. When the present compound contains a double bond, the present compound may exist in the form of geometric isomerism (cis-compound, trans-compound), and when the present compound contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization. In addition, the present compound includes an intramolecular salt, hydrate, solvate or polymorphism thereof.

Furthermore, suitable drug compounds are those that exert a local physiological effect, or a systemic effect, either after penetrating the mucosa or—in the case of oral administration—after transport to the gastrointestinal tract with saliva. The dosage forms prepared from the formulations according to the present invention are particularly suitable for drug compounds that exert their activity during an extended period of time, in particular drugs that have a half-life of at least several hours.

Synthesis Routes & Purification

An "isolated" peptide is a peptide substantially free of or separated from cellular material or other contaminating proteins from the cell or tissue source from which the peptide is produced and isolated, or substantially free of chemical precursors or other chemicals when the peptide is chemically synthesized. For example, protein that is substantially free of cellular material can include preparations of protein having less than about 30%, or preferably 20%, or more preferably 10%, or even more preferably 5%, or yet more preferably 1% (by dry weight), of contaminating proteins.

In preferred embodiments, the isolated peptide is substantially pure. Thus, when the peptide is recombinantly produced, it is substantially free of culture medium, e.g., culture medium representing less than about 20%, or more preferably 10%, or even more preferably 5%, or yet more preferably 1%, of the volume of the protein preparation. When the protein is produced by chemical synthesis, it is substantially free of chemical precursors or other chemicals, i.e., it is separated from chemical precursors or other chemicals that are involved in the synthesis of the protein. Accordingly such preparations of the peptide have less than about 30%, or preferably 20%, or more preferably 10%, or even more preferably 5%, or yet more preferably 1')/0 (by dry weight), of chemical precursors or compounds other than the peptide of interest.

Recombinant Production

Peptide expression in cellular environments may be achieved by the utilization of isolated polynucleotides. An "isolated" polynucleotide is one that is substantially separated from or free of nucleic acid molecules with differing nucleic acid sequences. Embodiments of isolated polynucleotide molecules include cDNA, genomic DNA, RNA, and anti-sense RNA. Preferred polynucleotides are obtained from biological samples derived from a human, such as from tissue specimens.

Vectors may be used to deliver and propagate polynucleotides encoding the peptide of SEQ ID NO:1. Introduction of such vectors into host cells may yield production of the encoded mRNA or protein of the mimetic stresscopin. Alternatively, expression vectors may be combined with purified elements including but not limited to transcription factors, RNA polymerase, ribosomes, and amino acids to produce efficient transcription/translation reactions in cell free conditions. Mimetic stresscopin peptides expressed from the resulting reactions may be isolated for further purification, modification, and/or formulation.

The term vector refers to a nucleic acid molecule capable of transporting another nucleic acid to which it has been linked. An exemplary type of vector is a plasmid, which refers to a circular double-stranded DNA loop into which additional DNA segments can be inserted. Another example of a vector is a viral vector wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors-expression vectors—are capable of directing the expression of genes to which they are operably linked. Vectors of utility in recombinant DNA techniques may be in the form of plasmids. Alternatively, other forms of vectors, such as viral vectors (e.g. replication defective retroviruses, adenoviruses and adeno-associated viruses), which serve equivalent functions, may be selected by the artisan as suitable for the intended use.

A host cell refers to a cell that contains a DNA molecule either on a vector or integrated into a cell chromosome. A host cell can be either a native host cell that contains the DNA molecule endogenously or a recombinant host cell. One example of a host cell is a recombinant host cell, which is a cell that has been transformed or transfected by an exogenous DNA sequence. A cell has been transformed by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA. A clone refers to a population of cells derived from a single cell or common ancestor by mitosis. A cell line refers to a clone of a primary cell that is capable of stable growth in vitro for many generations. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm derived cell lines. A recombinant host cell refers not only to the particular subject cell, but also to the progeny or potential progeny of such a cell. Particularly because certain modifications can occur in succeeding generations due to either mutation or environmental influences, such progeny may not be identical to the parent cell, but are still intended to be included within the scope of the term.

Illustrative vectors of the present invention also include specifically designed expression systems that allow the shuttling of DNA between hosts, such as bacteria-yeast or bacteria-animal cells or bacteria-fungal cells or bacteria-invertebrate cells. Numerous cloning vectors are known to those skilled in the art and the selection of an appropriate cloning vector is within the purview of the artisan. For other suitable expression systems for both prokaryotic and eukaryotic cells see, e.g., chapters 16 and 17 of Maniatis et al., (1990), "Molecular Cloning: A Laboratory Manual," vol. 2:16.3-16.81.

In order to obtain high level expression of a cloned gene or nucleic acid, such as a cDNA encoding a mimetic stresscopin peptide, a nucleotide sequence corresponding to the mimetic stresscopin peptide sequence is preferably subcloned into an expression vector that contains a strong promoter to direct transcription, a transcription/translation terminator, and if for a nucleic acid encoding a protein, a ribosome binding site for translational initiation. Suitable bacterial promoters are known in the art and are described, e.g., by Sambrook et al., (1989), *MOLECULAR CLONING: A LABORATORY MANUAL*, Second Edition, Cold Spring Harbor Laboratory, Cold Spring Harbor, N.Y. and Macrides, 1996, *Microbiol. Rev.* 60(3):512-38. Bacterial expression systems for expressing the mimetic stresscopin proteins disclosed in the present invention are available in, e.g., *E. coli, Bacillus* sp., and *Salmonella* (Palva et al., 1983, *Gene,* 22:229-235; Mosbach et al., 1983, *Nature,* 302:543-545). Kits for such expression systems are commercially available. Eukaryotic expression systems for mammalian cells, yeast, and insect cells are known in the art and are also commercially available. In exemplary embodiments, the eukaryotic expression vector is a baculovirus vector, adenoviral vector, an adeno-associated vector, or a retroviral vector.

A promoter refers to a regulatory sequence of DNA that is involved in the binding of RNA polymerase to initiate transcription of a gene. Promoters are often upstream (i.e., 5') to the transcription initiation site of the gene. A gene refers to a segment of DNA involved in producing a peptide, peptide, or protein, including the coding region, non-coding regions preceding (5'UTR) and following (3'UTR) coding region, as well as intervening non-coding sequences (introns) between individual coding segments (exons). Coding refers to the specification of particular amino acids or termination signals in three-base triplets (codons) of DNA or mRNA.

The promoter used to direct expression of the polynucleotide may be routinely selected to suit the particular application. The promoter is optionally positioned about the same distance from the heterologous transcription start site as it is from the transcription start site in its natural setting. As will be apparent to the artisan, however, some variation in this distance can be accommodated without loss of promoter function.

In addition to the promoter, the expression vector may contain a transcription unit or expression cassette that contains all the additional elements required for the expression of the mimetic stresscopin-encoding polynucleotide in host cells. An exemplary expression cassette contains a promoter operably linked to the polynucleotide sequence encoding a mimetic stresscopin peptide, and signals required for efficient polyadenylation of the transcript, ribosome binding sites, and translation termination. The polynucleotide sequence encoding a canine mimetic stresscopin peptide may be linked to a cleavable signal peptide sequence to promote secretion of the encoded protein by the transfected cell. Exemplary signal peptides include the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence, the human stresscopin gene, or may be obtained from different genes.

In exemplary embodiments, any of the vectors suitable for expression in eukaryotic or prokaryotic cells known in the art may be used. Exemplary bacterial expression vectors include plasmids such as pBR322-based plasmids, pSKF, pET23D, and fusion expression systems such as GST and LacZ. Examples of mammalian expression vectors include, e.g., pCDM8 (Seed, 1987, *Nature,* 329:840) and pMT2PC (Kaufman et al., 1987, *EMBO J.,* 6:187-195). Commercially available mammalian expression vectors which can be suitable for recombinant expression of peptides of the invention include, for example, pMAMneo (Clontech, Mountain View, Calif.), pcDNA4 (Invitrogen, Carlsbad, Calif.), pCiNeo (Promega, Madison, Wis.), pMC1neo (Stratagene, La Jolla, Calif.), pXT1 (Stratagene, La Jolla, Calif.), pSG5 (Stratagene, La Jolla, Calif.), EBO-pSV2-neo (ATCC 37593), pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Epitope tags may also be added to recombinant proteins to provide convenient methods of isolation, e.g., c-myc, hemoglutinin (HA)-tag, 6-His tag, maltose binding protein, VSV-G tag, or anti-FLAG tag, and others available in the art.

Expression vectors containing regulatory elements from eukaryotic viruses may be used in eukaryotic expression vectors, e.g., SV40 vectors, papilloma virus vectors, and vectors derived from Epstein-Barr virus. Other exemplary eukaryotic vectors include pMSG, pAV009/A+, pMT010/A+, pMAMneo 5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding a mimetic stresscopin peptide under the direction of the polyhedrin promoter or other strong baculovirus promoters.

Elements that can be included in expression vectors also include a replicon that functions in *E. coli*, a gene encoding antibiotic resistance to permit selection of bacteria that harbor recombinant plasmids, and unique restriction sites in nonessential regions of the plasmid to allow controlled insertion of eukaryotic sequences. The particular antibiotic resistance gene may be selected from the many resistance genes known in the art. The prokaryotic sequences may be chosen such that they do not interfere with the replication of the DNA in eukaryotic cells, if necessary or desired.

Known transfection methods may be used to produce bacterial, mammalian, yeast or insect cell lines that express large quantities of a SCP mimetic, which are then purified using standard techniques, such as selective precipitation with such substances as ammonium sulfate, column chromatography, and immunopurification methods.

Transformation of eukaryotic and prokaryotic cells may be performed according to standard techniques (see, e.g., Morrison, 1977*, J. Bact.,* 132:349-351; Clark-Curtiss & Curtiss, *Methods in Enzymology,* 101:347-362).

Any of the known procedures suitable for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the Gene Gun), or any other known methods for introducing cloned genomic DNA, cDNA, synthetic DNA or other foreign genetic material into a host cell (see, e.g., Sambrook et al., supra). The particular genetic engineering procedure selected should be capable of successfully introducing at least one gene into the host cell capable of expressing a mimetic stresscopin RNA, mRNA, cDNA, or gene.

As would be apparent to artisans, for stable transfection of mammalian cells, depending upon the expression vector and transfection technique used, only a small fraction of cells may integrate the foreign DNA into their genome. In order to identify and select these integrants, a gene that encodes a selectable marker (e.g., for resistance to antibiotics) may be introduced into the host cells along with the gene of interest. Exemplary selectable markers include those which confer resistance to drugs, such as G-418, puromycin, geneticin, hygromycin and methotrexate. Cells stably transfected with the introduced nucleic acid can be selected for and identified by drug selection (e.g., cells that have incorporated the selectable marker gene will survive, while the other cells die).

A heterologous regulatory element may be inserted into a stable cell line or cloned microorganism, such that it is operatively linked with and activates expression of endogenous genes, using techniques such as targeted homologous recombination, e.g., as described in U.S. Pat. No. 5,272,071 and International Publication No. WO 91/06667. After the expression vector is introduced into the cells, the transfected cells are preferably cultured under conditions optimally favoring expression of the mimetic stresscopin peptide, which is recovered from the culture using standard techniques identified below. Methods of culturing prokaryotic or eukaryotic cells are known in the art; see, e.g., Sambrook et al., supra; Freshney, 1993*, CULTURE OF ANIMAL CELLS,* 3rd ed.

As an alternative to using cellular systems for peptide production, cell-free systems have shown the capability for gene expression and synthesis in prokaryotic (Zubay G., *Annu Rev Genet.,* 1973, 7:267-287) and eukaryotic systems (Pelham et al., *Eur J. Biochem.,* 1976, 67:247-256; Anderson et al., *Meth Enzymol.,* 1983, 101:635-644). These systems can utilize either mRNA or DNA nucleotides for peptide synthesis reactions. A preferred technique for cell-free peptide production uses reticulocyte lysate, RNA polymerase, nucleotides, salts, and ribonuclease inhibitor in one quick coupled transcription/translation reaction (TNT®, Promega, Madison, Wis., U.S.A.).

Synthetic Production Peptides as embodied in the invention may be prepared using the solid-phase synthetic technique initially described by Merrifield, in J. Am. Chem. Soc., 15:2149-2154 (1963). Other peptide synthesis techniques may be found, for example, in M. Bodanszky et al., (1976) *Peptide Synthesis*, John Wiley & Sons, 2d Ed.; Kent and Clark-Lewis in *Synthetic Peptides in Biology and Medicine*, p. 295-358, eds. Alitalo, K., et al. *Science Publishers*, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105-237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Block synthesis techniques may also be applied to both the solid phase and solution methods of peptide synthesis. Rather than sequential addition of single amino acid residues, preformed blocks comprising two or more amino acid residues in sequence are used as either starting subunits or subsequently added units rather than single amino acid residues.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Solid support synthesis may be achieved with automated protein synthesizers (Protemist®, CellFree Sciences, Matsuyama Ehime 790-8577, Japan; Symphony SMPS-110, Rainin, Woburn, Mass., U.S.A.; ABI 433A peptide synthesizer, Applied Biosystems, Foster City, Calif., U.S.A.). Such machines have the capability to perform automated protein reactions that allow for greater control and optimization of the synthesis.

Purification

A number of procedures may be employed to isolate or purify the inventive peptide. For example, column chromatography may be used to purify peptides based on their physical properties, i.e. hydrophobicity. Alternatively, proteins having established molecular adhesion properties may be reversibly fused to the inventive peptide. With an appropriate ligand for the fused protein, the mimetic stresscopin peptide may be selectively adsorbed to a purification column and then freed from the column in a substantially pure form. The fused protein may then be removed by enzymatic activity. Alternative column purification strategies may employ antibodies raised against the mimetic stresscopin peptide. These antibodies may be conjugated to column matrices and the peptides purified via these immunoaffinity columns.

Recombinant proteins may be separated from the host reactions by suitable separation techniques such as salt fractionation. This method may be used to separate unwanted host cell proteins (or proteins derived from the cell culture media) from the recombinant protein of interest. An exemplary salt is ammonium sulfate, which precipitates proteins by effectively reducing the amount of water in the protein mixture (proteins then precipitate on the basis of their solubility). The more hydrophobic a protein is, the more likely it is to precipitate at lower ammonium sulfate concentrations. An exemplary isolation protocol includes adding saturated ammonium sulfate to a protein solution so that the resultant ammonium sulfate concentration is between 20-30%, to precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed to achieve the desired purity, e.g., through dialysis or diafiltration. Other known methods that rely on solubility of proteins, such as cold ethanol precipitation, may be used to fractionate complex protein mixtures.

In other examples of isolation or purification techniques, the molecular weight of the inventive peptide may be used to isolate it from proteins of greater and lesser size using ultrafiltration through membranes of different pore size (for example, Amicon or Millipore membranes). As a first step, the protein mixture is ultra-filtered through a membrane with a pore size that has a lower molecular weight cut-off than the molecular weight of the protein of interest. The retained matter of the ultrafiltration is then ultrafiltered against a membrane with a molecular cut-off greater than the molecular weight of the protein of interest. The recombinant protein will pass through the membrane into the filtrate, and the filtrate may then be chromatographed.

Chemical Modifications

The inventive peptide may be subjected to directed chemical modifications, such as maleimide capping, polyethylene glycol (PEG) attachment, maleidification, acylation, alkylation, esterification, and amidification, to produce structural analogs of the peptide. One skilled in the art would appreciate the existence of a variety of chemical modification techniques and moieties, see for example U.S. Pat. Nos. 5,554,728, 6,869,932, 6,828,401, 6,673,580, 6,552,170, 6,420,339, U.S. Pat. Pub. 2006/0210526 and Intl. Pat. App. WO 2006/136586. Preferably, chemical modifications are performed on isolated peptide, e.g., to increase reaction efficiencies.

In certain embodiments of the invention, the inventive peptide contains an amidated C-terminus. Such peptide modification procedures may be performed on isolated purified peptide or, as in the case of solid-phase synthesis, may be performed during the synthesis procedure. Such procedures are reviewed in Ray et al., *Nature Biotechnology*, 1993, vol. 11, pp. 64-70; Cottingham et al., *Nature Biotechnology*, 2001, vol. 19, pp. 974-977; Walsh et al., *Nature Biotechnology*, 2006, vol. 24, pp. 1241-1252; U.S. Pat. Appl. Publ. 2008/0167231.

The peptides of the invention may contain certain intermediate linkers that are useful to bind the peptide and a PEG moiety. Such linkers would convey minimal immunogenicity and toxicity to the host. Examples of such linkers may be found in Bailon et al., *PSTT,* 1998, vol. 1(8), pp. 352-356.

In certain embodiments, the invention is directed to a conjugate comprising an isolated peptide consisting essentially of a sequence as set forth in SEQ ID NO:29 containing a $CONH_2$ at its carboxy terminus and a intermediate linker conjugated to the cysteine residue at position 28 of the amino acid sequence of SEQ ID NO:29. In certain embodiments, the intermediate linker is N-ethylsuccinimide. In further embodiments the intermediate linker may be vinyl sulphone. In further embodiments, the intermediate linker may be acetamide. In certain embodiments, the intermediate linker may be orthopyridyl disulfide.

In further embodiments, the invention is directed towards a conjugate comprising a peptide having the amino acid sequence as set forth in SEQ ID NO:29 with a $CONH_2$ at its carboxy terminus, an N-ethylsuccinimide linker conjugated to the cysteine residue at position 28 of SEQ ID NO:29, wherein the N-ethylsuccinimide linker is also bound to a PEG moiety. In certain embodiments, the molecular weight of the PEG moiety may range from about 2 kDa to about 80 kDa. In certain embodiments, the mass of the PEG is about 20 kDa. In preferred embodiments, the CRHR2 peptide agonist comprises a peptide of SEQ ID NO:82 or SEQ ID NO:102. In certain embodiments, the PEG mass is about 5 kDa. In certain other embodiments, the PEG mass is about 12 kDa. In certain embodiments, the PEG mass is about 20 kDa. In certain embodiments, the PEG is mass about 30 Da. In certain embodiments, the PEG mass is about 40 kDa. In certain embodiments, the PEG mass is about 80 kDa. In certain embodiments, the PEG moiety is linear. In other embodiments, the PEG moiety is branched. PEG moieties may be synthesized according to methods known to one of ordinary skilled in the art. Alternatively, PEG moieties are commercially available, such as SUNBRIGHT® ME-020MA, SUNBRIGHT® ME-050MA, and SUN-BRIGHT® ME-200MA (NOF corp., Japan; Sigma Aldrich, St. Louis, Mo., U.S.A.)

The invention further relates to pharmaceutically acceptable salts of the inventive peptide and methods of using such salts. A pharmaceutically acceptable salt refers to a salt of a free acid or base of the peptide that is non-toxic, biologically tolerable, or otherwise biologically suitable for administration to the subject. See, generally, S. M. Berge, et al., "Pharmaceutical Salts", *J. Pharm. Sci.,* 1977, 66:1-19, and Handbook of *Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A peptide may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive peptide contains a basic nitrogen, the desired pharmaceutically acceptable salt may be prepared by any suitable method available in the art, for example, treatment of the free base with an inorganic acid, such as hydrochloric acid, hydrobromic acid, hydriodic acid, perchloric acid, sulfuric acid, sulfamic acid, nitric acid, boric acid, phosphoric acid, and the like, or with an organic acid, such as acetic acid, trifluoroacetic acid, phenylacetic acid, propionic acid, stearic acid, lactic acid, ascorbic acid, maleic acid, hydroxymaleic acid, malic acid, pamoic acid, isethionic acid, succinic acid, valeric acid, fumaric acid, saccharinic acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, benzenesulfonic acid, 2-naphthalenesulfonic acid, p-toluenesulfonic acid, methanesulfonic acid, ethanesulfonic acid, hydroxyethanesulfonic, a cyclohexanesulfamic acid, any compatible mixture of acids such as those given as examples herein, and any other acid and mixture thereof that are regarded as equivalents or acceptable substitutes in light of the ordinary level of skill in this technology.

If the inventive peptide contains an acid group, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium. Representative organic or inorganic bases further include benzathine, chloroprocaine, choline, diethanolamine, ethylenediamine, meglumine, and procaine.

The invention also relates to pharmaceutically acceptable prodrugs of the compounds, and treatment methods employing such pharmaceutically acceptable prodrugs. The term "prodrug" means a precursor of a designated compound that, following administration to a subject yields the compound in vivo via a chemical or physiological process such as solvolysis or enzymatic cleavage, or under physiological conditions. A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of the compound. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of the compound as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)-methyl and (acyloxy)-ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Greenwald, et al., *J Med. Chem.* 1996, 39, 10, 1938-40. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds, which may also be used in the methods of the invention. A "pharmaceutically active metabolite" means a pharmacologically active product of metabolism in the body of the compound or salt thereof. Prodrugs and active metabolites of a compound may be determined using routine techniques known or available in the art. See, e.g., Bertolini, et al., *J Med. Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

Pharmaceutical Compositions

In particular embodiments of the invention, CRHR2 peptide agonists are used alone, or in combination with one or more additional ingredients, to formulate pharmaceutical compositions. A pharmaceutical composition comprises an effective amount of at least one compound in accordance with the invention.

In some embodiments, the pharmaceutical composition comprises a peptide having the amino acid sequence as set forth in SEQ ID NO:29, wherein the peptide contains a $CONH_2$ at its carboxy terminus, and further comprises a N-ethylsuccinimide or acetamide linker attached to the cysteine residue at position 28, wherein said linker is also linked to a PEG moiety. PEG moieties are classified by their molecular weight and physical characteristics, such as being linear or branched, and containing one or more linker moieties used to bond the PEG to the peptide substrate. In certain preferred embodiments, the peptide contains one or two said linkers.

In certain embodiments, the pharmaceutical composition comprising the PEG moiety may contain a PEG moiety whose weight may range between about 2 kDa to about 80 kDa. In certain embodiments, the PEG moiety mass is about 2 kDa. In further embodiments, the PEG mass is about 5 kDa. In certain embodiments, the PEG mass is about 12 kDa. In certain embodiments, the PEG mass is about 20 kDa. In certain embodiments, the PEG mass is about 30 kDa. In certain embodiments, the PEG mass is about 40 kDa. In certain embodiments, the PEG mass is about 80 kDa. Such compositions may further comprise a pharmaceutically acceptable excipient.

The disclosure also provides compositions (including pharmaceutical compositions) comprising a compound or derivatives described herein, and one or more of pharmaceutically acceptable carrier, excipient, and diluent. In certain embodiments of the invention, a composition may also contain minor amounts of wetting or emulsifying agents, or pH buffering agents. In a specific embodiment, the pharmaceutical composition is pharmaceutically acceptable for administration to a human. In certain embodiments, the pharmaceutical composition comprises a therapeutically or prophylactically effective amount of a compound or derivative described herein. The amount of a compound or derivative of the invention that will be therapeutically or prophylactically effective can be determined by standard clinical techniques. Exemplary effective amounts are described in more detail in below sections. In certain embodiments of the invention, a composition may also contain a stabilizer. A stabilizer is a compound that reduces the rate of chemical degradation of the modified peptide of the composition. Suitable stabilizers include, but are not limited to, antioxidants, such as ascorbic acid, pH buffers, or salt buffers.

The pharmaceutical compositions can be in any form suitable for administration to a subject, preferably a human subject. In certain embodiments, the compositions are in the form of solutions, suspensions, emulsion, tablets, pills, capsules, powders, and sustained-release formulations. The compositions may also be in particular unit dosage forms. Examples of unit dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

In a specific embodiment, the subject is a mammal such as a cow, horse, sheep, pig, fowl, cat, dog, mouse, rat, rabbit, or guinea pig. In a preferred embodiment, the subject is a human. Preferably, the pharmaceutical composition is suitable for veterinary and/or human administration. In accordance with this embodiment, the term "pharmaceutically acceptable" means approved by a regulatory agency of the Federal or a state government or listed in the U.S. Pharmacopeia or other generally recognized pharmacopeia for use in animals, and more particularly for use in humans.

Suitable pharmaceutical carriers for use in the compositions are sterile liquids, such as water and oils, including those of petroleum, animal, vegetable or synthetic origin. In a specific embodiment, the oil is peanut oil, soybean oil, mineral oil, or sesame oil. Water is a preferred carrier when the pharmaceutical composition is administered intravenously. Saline solutions and aqueous dextrose and glycerol solutions can also be employed as liquid carriers, particularly for injectable solutions. Further examples of suitable pharmaceutical carriers are known in the art, e.g., as described by E. W. Martin in *Remington's Pharmaceutical Sciences* (1990) 18th ed. (Mack Publishing, Easton Pa.).

Suitable excipients for use in the compositions include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. Whether a particular excipient is suitable for incorporation into a pharmaceutical composition depends on a variety of factors well known in the art including, but not limited to, the route of administration and the specific active ingredients in the composition.

In certain embodiments of the invention, a composition is an anhydrous composition. Anhydrous compositions can be prepared using anhydrous or low moisture containing ingredients and low moisture or low humidity conditions. Compositions comprising modified peptides having a primary or secondary amine are preferably anhydrous if substantial contact with moisture and/or humidity during manufacturing, packaging, and/or storage is expected. An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Pharmaceutical compositions comprising the compounds or derivatives described herein, or their pharmaceutically acceptable salts and solvates, are formulated to be compatible with the intended route of administration. The formulations are preferably for subcutaneous administration, but can be for administration by other means such as by inhalation or insufflation (either through the mouth or the nose), intradermal, oral, buccal, parenteral, vaginal, or rectal. Preferably, the compositions are also formulated to provide increased chemical stability of the compound during storage and transportation. The formulations may be lyophilized or liquid formulations.

In one embodiment, the compounds or derivatives are formulated for intravenous administration. Intravenous formulations can include standard carriers such as saline solutions. In another embodiment, the compounds or derivatives are formulated for injection. In a preferred embodiment, the compounds or derivatives are sterile lyophilized formulations, substantially free of contaminating cellular material, chemicals, virus, or toxins. In a particular embodiment, the compounds or derivatives are formulated in liquid form. In another particular embodiment, formulations for injection are provided in sterile single dosage containers. In a particular embodiment, formulations for injection are provided in sterile single dosage containers. The formulations may or may not contain an added preservative. Liquid formulations may take such forms as suspensions, solutions or emulsions in oily or aqueous vehicles, and may contain formulation agents such as suspending, stabilizing and/or dispersing agents.

Methods of Administration

A compound or derivative described herein, or a pharmaceutically acceptable salt thereof, is preferably administered as a component of a composition that optionally comprises a pharmaceutically acceptable vehicle. The compound or derivative is preferably administered subcutaneously. Another preferred method of administration is via intravenous injection or continuous intravenous infusion of the compound or derivative. Preferably, the administration is reaching a steady state in blood plasma levels by slow systemic absorption and clearance of the compound or derivative or maintaining a blood plasma concentration level in a defined range over a period of time.

In certain embodiments, the compound or derivative is administered by any other convenient route, for example, by infusion or bolus injection, or by absorption through epithelial or mucocutaneous linings (e.g., oral mucosa, rectal, and intestinal mucosa). Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In most instances, administration will result in the release of the compound or derivative into the bloodstream.

The preparation may be in the form of tablets, capsules, sachets, dragees, powders, granules, lozenges, powders for reconstitution, liquid preparations, or suppositories. Preferably, the compositions are formulated for intravenous infusion or bolus injection, subcutaneous infusion or bolus injection, or intra muscular injection.

The compound is preferably administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution, dextrose solution, and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may be given over a period ranging from several minutes to several days. In yet another embodiment, an effective amount of the inventive peptide may be coated on nanoparticles or provided in a "depot" suitable for subcutaneous delivery (Hawkins et al., *Adv Drug Deliv Rev.*, 2008, vol. 60, pp. 876-885; Montalvo et al., *Nanotechnology*, 2008, vol. 19, pp. 1-7).

Active agents may be administered through inhalation methods. Such methods may use dry powder (Johnson K. A., *Adv Drug Del Rev.*, 1997, vol. 26(1), pp. 3-15) and/or aerosol (Sangwan et al., *J Aerosol Med.*, 2001, vol. 14(2), pp. 185-195; Int. Pat. Appl. WO2002/094342) formulation techniques.

In embodiments of treatment methods according to the invention, a therapeutically effective amount of at least one active agent according to the invention is administered to a subject suffering from or diagnosed as having such a disease, disorder, or condition, such as heart failure, diabetes, skeletal muscle wasting, and sarcopenia. Additional conditions include improper motor activity, food intake, or a need for cardioprotective, bronchorelaxant, and/or anti-inflammatory activity. Therapeutically effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary intravenous dose rate is in the range from about 0.2 ng to about 52 ng of stresscopin-relative active agent per kg of subject's body weight per minute, preferably about 0.2 ng/kg/min to about 22 ng/kg/min, or equivalently about 0.3 µg/kg to about 32 µg/kg daily. In the case of bolus infusion or subcutaneous injection, the total dose can be administered in single or divided dosage units (e.g., BID, TID, QID, twice-a-week, biweekly or monthly). For a 70-kg human, an illustrative range for a suitable dosage amount is from about 1 µg/day to about 1 mg/day. Weekly dosage regiments can be used as an alternate to daily administration. In another preferred embodiment, the CRHR2 peptide agonist of SEQ ID NO:102, which comprises an acetamide linker binding a PEG of about 20 kDa to the cysteine residue at position 28 of the peptide sequence, is administered at a dose of 10 µg/kg by bolus subcutaneous injection to a patient in need thereof. The frequency of this dosage should range from once a day to less frequent based upon the therapeutic needs of the subject and other clinical considerations.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. If symptoms have been alleviated to an appropriate level, treatment may cease. Patients may, however, require intermittent treatment on a long-term basis upon any recurrence of symptoms.

In certain embodiments, the compound is administered in combination with one or more other biologically active agents as part of a treatment regimen. In certain embodiments, the compound is administered prior to, concurrently with, or subsequent to the administration of the one or more other biologically active agents. In one embodiment, the one or more other biologically active agents are administered in the same pharmaceutical composition with a compound as described herein. In another embodiment, the one or more other biologically active agents are administered in a separate pharmaceutical composition with a compound as described herein. In accordance with this embodiment, the one or more other biologically active agents may be administered to the subject by the same or different routes of administration as those used to administer the compound.

In another embodiment, the compound is administered with one or more other compound or composition for reducing risk or treating a cardiovascular disease. Compounds or compositions that reduce the risk or treat cardiovascular disease include, but are not limited to, anti-inflammatory agents, anti-thrombotic agents, anti-platelet agents, fibrinolytic agents, thrombolytics, lipid reducing agents, direct thrombin inhibitors, anti-Xa inhibitors, anti-IIa inhibitors, glycoprotein IIb/IIIa receptor inhibitors and direct thrombin inhibitors. Examples of agents that can be administered in combination with the compound as described herein include bivalirudin, hirudin, hirugen, Angiomax, agatroban, PPACK, thrombin aptamers, aspirin, GPIIb/IIIa inhibitors (e.g., Integrelin), P2Y12 inhibitors, thienopyridine, ticlopidine, and clopidogrel.

In embodiments, the compound is formulated into dosage forms suitable for administration to patients in need thereof. The processes and equipment for preparing drug and carrier particles are disclosed in *Pharmaceutical Sciences*, Remington, 17th Ed., pp. 1585-1594 (1985); *Chemical Engineers Handbook*, Perry, 6th Ed., pp. 21-13 to 21-19 (1984); *Journal of Pharmaceutical Sciences*, Parrot, Vol. 61, No. 6, pp. 813-829 (1974); and *Chemical Engineer*, Nixon, pp. 94-103 (1990).

The amount of compound incorporated in the dosage forms of the present invention may generally vary from about 10% to about 90% by weight of the composition depending upon the therapeutic indication and the desired administration period, e.g., every 12 hours, every 24 hours, and the like. Depending on the dose of compound desired to be administered, one or more of the dosage forms can be administered. Depending upon the formulation, the compound will preferably be in the form of an HCl salt or free base form.

Further, this invention also relates to a pharmaceutical composition or a pharmaceutical dosage form as described hereinbefore for use in a method of therapy or diagnosis of the human or non-human animal body.

This invention also relates to a pharmaceutical composition for use in the manufacture of a pharmaceutical dosage form for oral administration to a mammal in need of treatment, characterized in that said dosage form can be administered at any time of the day independently of the food taken in by said mammal.

This invention also relates to a method of therapy or diagnosis of the human or non-human animal body that comprises administering to said body a therapeutically or diagnostically effective dose of a pharmaceutical composition described herein.

This invention also relates to a pharmaceutical package suitable for commercial sale comprising a container, a dosage form as described herein, and associated with said package written matter non-limited as to whether the dosage form can be administered with or without food.

The following formulation examples are illustrative only and are not intended to limit the scope of the inventions in any way.

EXAMPLES

Example 1: Synthesis and Purification of Peptide

The peptide of SEQ ID NO:29 was prepared by a solid phase peptide synthesis reaction on a Rainin Symphony Multiple Peptide Synthesizer (Model SMPS-110) using software version 3.3.0. Resin (NovaSyn TGR®, 440 mg, approximately 0.1 mmole, 0.23 mmol/g substitution, Lot No. A33379) used for the synthesis of peptide amides was a composite of polyethylene glycol and polystyrene functionalized with an acid-labile modified Rink amide linker.

Amino acids used in synthesis contained Na-9-Fluorenylmethoxycarbonyl (Fmoc) protection groups on the C-terminus and the following side-chain protecting groups: Arg(2, 2,4,6,7-pentamethyldihydrobenzofuran-5-sulfonyl, pbf), Asp(tertiary butoxy, OtBu), Asn(Trityl, Trt), Gln(Trt), Cys (Trt), His(Trt), Lys(t-Butoxycarbonyl, Boc), Ser(tertiary butyl, tBu) and Thr(tBu).

Coupling reactions were carried out by mixing N-Methylpyrrolidinone (NMP) pre-swollen resin (0.1 mmole), a 5-fold molar excess of Fmoc-amino acid in DMF (2.5 mL) and 5-fold molar excess of hexafluorophosphate (HBTU) with a 10-fold molar excess of N-Methylmorpholine (NMM) in DMF (2.5 mL) were added, then coupled for over 45 minutes. For Fmoc removal, reactions were incubated with a 20% Piperidine/DMF solution for 2 minutes. The solution was then drained and fresh 20% Piperidine/DMF was added and incubated for 18 minutes. Reactions were then washed with NMP and subsequent amino acid additions performed by repeat of coupling steps. For C-terminal coupling to Ile40, Gln39, Asn19, Asn12, and Val9 numbered from the N-terminus, the coupling steps were performed twice.

Peptide cleavage from the resin was performed using a two-hour cleavage program and incubation with 9 mL of a cleavage mixture comprising trifluoroacetic acid (TFA) (100 mL), 1,2-ethanedithiol (EDT) (20.0 mL), phenol (7.5 g), thioanisole (5 mL), triisopropylsilane (TIS) (5 mL) and water (5 mL). The solution of cleaved peptide was transferred to a 50-mL BD polypropylene centrifuge tube, and the peptide was precipitated with cold ethyl ether (40 mL). The mixture was centrifuged, and the ethyl ether was decanted from the peptide. Ethyl ether (40 mL) was added, the mixture was vortexed and centrifuged, and the ethyl ether was decanted. These steps (addition of fresh ethyl ether, vortexing, centrifugation, and decanting) were repeated two additional times. The peptide was dried in vacuo to give 408 mg (92% yield) of the crude product.

Peptide purification was performed on a Waters preparative HPLC system (Waters, Mass., U.S.A.). The crude peptide (~100 mg) was dissolved in 20/30/50 acetic acid/acetonitrile/water containing 0.1% TFA. The material injected onto two Vydac C-18 columns (10 mm, 2.5×25 cm). After the injection, a gradient of 0-45% solvent (solvent B=80% acetonitrile containing 0.1% TFA) over 5 min and 45-70% solvent B over 60 min with a flow rate of 6 mL/min was utilized to purify the peptide. Fractions were collected and analyzed by analytical RP-HPLC, MALDI-TOF MS, and CE. The most pure fractions were pooled and lyophilized to give 23 mg of product. MALDI-TOF MS yielded molecular weight of the product to equal 4400.5, which is larger than the calculated molecular weight for $C_{195}H_{326}N_{56}O_{53}S_3$ of 4399.2 by one hydrogen atom. Lyophilization was made by flash freezing the liquid in an acetone dry ice bath for approximately 30 minutes. After freezing, the product, in an open flask, was covered with filter paper and placed under high vacuum. After 24 hours under high vacuum dried sample was removed from vacuum and storage container sealed for future use.

Example 2: Conjugation of Peptide with N-Ethylmaleimide

Site directed N-ethylmaleimide capping on cysteine residues as shown in Scheme 1 was achieved under the conditions as follows.

Scheme 1

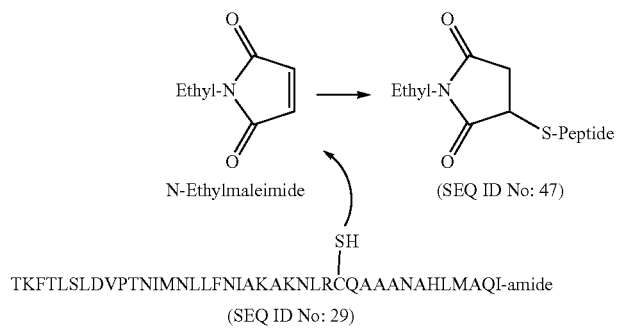

N-Ethylmaleimide (SEQ ID No: 47)

SH
|
TKFTLSLDVPTNIMNLLFNIAKAKNLRCQAAANAHLMAQI-amide
(SEQ ID No: 29)

In a 2.5 mL polypropylene vial, 2.0 mg of the inventive peptide was dissolved in 1.0 mL water. Twenty microliters of 0.1M aqueous N-ethylmaleimide was then added immediately. The reaction was gently agitated at room temperature for 2 hours. The reaction mixtures were purified on a Summit APS (Dionex, CA, U.S.A.) HPLC fit with a Vydac C18 300 Angstrom, (10×250 mm; Grace Davison, IL, U.S.A.) column using the following protocol shown in Table 6. End Fractions were collected, analyzed by HPLC, and the pure fractions pooled and lyophilized.

TABLE 6

| Column: | Vydac C 18 300 Ångstrom (10 × 250 mm) |
|---|---|
| Solvents: | A: 0.1% TFA in Water |
|  | B: 0.1% TFA with 80% Acetonitrile/Water |
| UV: | (1) 214 nm |
|  | (2) 280 nm |
| Flow: | 2.000 ml/min at 0.000 min |
| Gradient (% B) at time: |  |
| 4.000 min | 0.0% |
| 40.000 min | 100.0% |
| 60.000 min | 100.0% |
| 62.000 min | 0.0% |
| 75.000 min | 0.0% |

Example 3: Conjugation of Peptide with Iodoacetamide-PEG

Iodoacetamide-PEG, a linear 20 kDa polyethylene glycol chain with an iodoacetamide terminus, and present in limiting quantities at slightly alkaline pH with peptide of SEQ ID NO:29 resulted in cysteine modification as an exclusive reaction as shown in Scheme 2. The cysteine thiol acted as a selective point of attachment for the iodacetamide-PEG. The resulting derivative alpha sulfahydrylacetamide linkage was achiral.

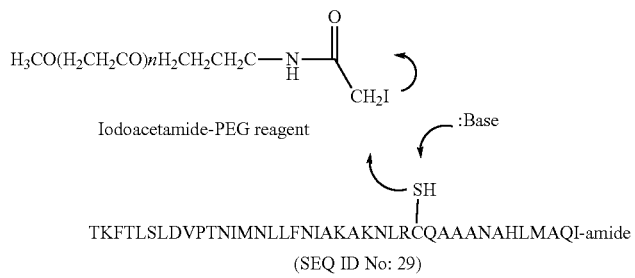

Scheme 2

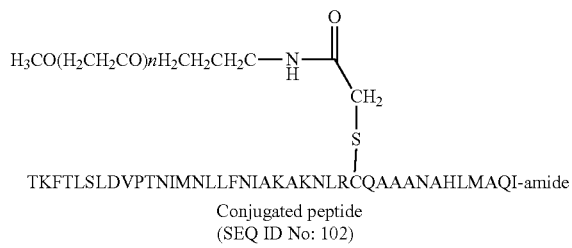

Figure 1B:
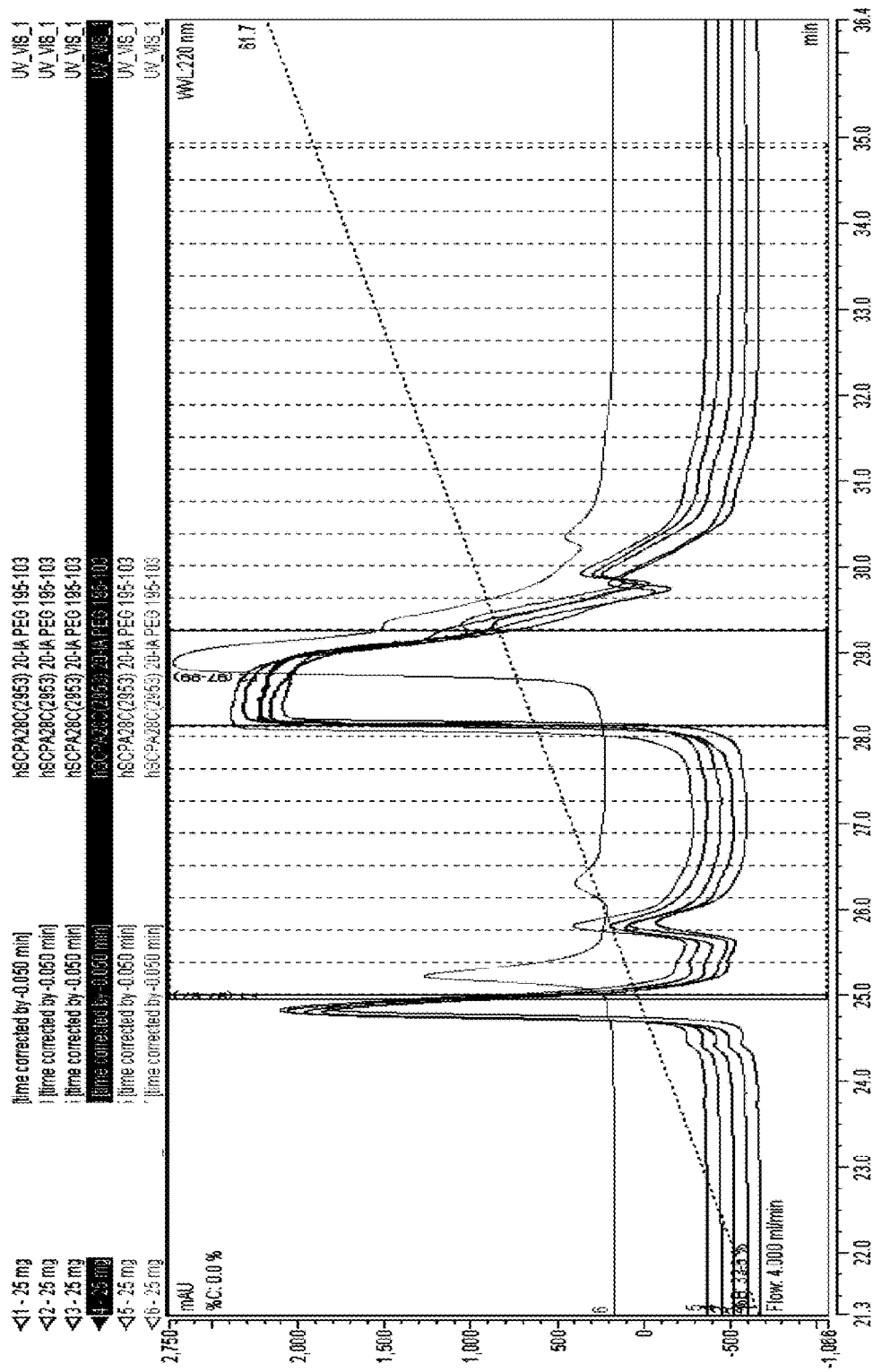
FIG. 1C shows the mass spectroscopy graph of a peptide agonist with SEQ ID NO:102 that was derivatized with iodoacetamide-PEG.

To a 15 mL conical flask, 25 mg (5.68 mmol, 1.0 eq) of peptide of SEQ ID NO:1 was added. Into the same flask 140 mg (6.82 mmol, 1.2 eq, 95% active) PEG-20 iodoacetamide (Lot No. M77592) made by Nippon, Oil and Fat (NOF) Corp. was added. 10 mL of water was added and the solution vortexed until all solids were dissolved. To the cloudy solution, 50 mL of pyridine was added at a solution pH of about 8.91. After 2 hours, a 20 mL aliquot of sample was removed and analyzed by reverse phase HPLC using a Phenomenex C6-phenyl column with 0.1% TFA/acetonitrile as eluents. The sample showed near complete reaction after 2 hours (FIG. 1A). The reaction mixture was purified directly by HPLC using a Phenomenex C6 phenyl 10×150 mm column. Eluents for purification were 0.1% TFA water and 80% acetonitrile in 0.1 TFA water. Purifications were in sample batches of 2-3 mL (FIG. 1B). Purified fractions were combined and lyophilized in a 50 mL conical flask. The lyophilized solid was diluted in 10 mL of water and re-lyophilized. Approximately 1 mg of the final product was diluted to 1 mg/mL and submitted for mass spectroscopic analysis (FIG. 1C). The average weight of the pegylated compound of SEQ ID NO:102 was 25,449 Dalton due in part to the heterogeneity in the length of the PEG polymer, and the compound appeared as a white amorphous solid.

Example 4: Pegylation of Peptide with N-Ethylmaleimide Linker

In a 2.5 mL polypropylene vial 2.0 mg (~0.44 nmol) of the peptide in was dissolved in 2.5 mL water followed by the immediate addition of activated and N-ethylmaleimide-derivatived polyethylene glycols of varying molecular weight by using the amounts shown in Table 7.

Scheme 3

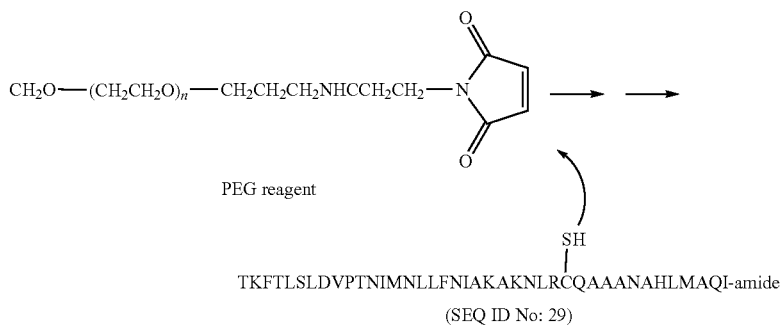

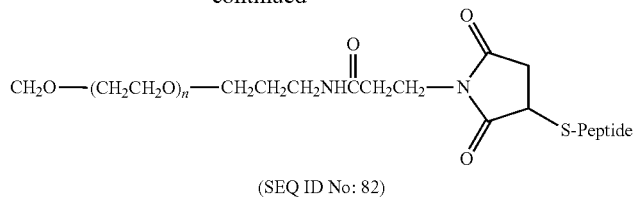

(SEQ ID No: 82)

The reaction mixture was gently agitated at room temperature for 2 hours.

TABLE 7

| PEG Structure | PEG-Malemide MW [kDa] | NOF Corp. Catalog No. | Amount [mg] |
|---|---|---|---|
| Linear | 2 | SUNBRIGHT ® ME-020MA | 1.0 mg (0.49 nMol) |
| Linear | 5 | SUNBRIGHT ® ME-050MA | 2.0 mg (0.49 nMol) |
| Linear | 12 | SUNBRIGHT ® ME-120MA | 6.0 mg (0.49 nMol) |
| Linear | 20 | SUNBRIGHT ® ME-200MA | 10.0 mg (0.49 nMol) |
| Linear | 30 | SUNBRIGHT ® ME-300MA | 15.0 mg (0.49 nMol) |
| Linear | 40 | SUNBRIGHT ® ME-400MA | 20.0 mg (0.49 nMol) |
| Branched | 80 | SUNBRIGHT ® GL2-800MA | 40.0 mg (0.49 nMol) |
| Double Ended Maleimide | 20 | SUNBRIGHT ® DE-200MA | 5.0 mg (0.49 nMol) |

The reaction mixtures were purified on a Summit APS (Dionex, CA, U.S.A.) HPLC fit with a Gemini 5u C6-phenyl 110 Angstrom (10×100 mm; Phenomenex, CA, U.S.A.) column using the protocol of Table 8.

TABLE 8

| Column: | Phenomenex Gemini 5u C6-phenyl 110 Ångstrom (10 × 100 mm) |
|---|---|
| Solvents: | A: 0.1% TFA in Water |
| | B: 0.1% TFA with 80% Acetonitrile/Water |
| UV: | (1) 214 nm |
| | (2) 280 nm |
| Flow: | 4.000 ml/min at 0.000 min |
| Gradient (% B) at time: | |
| 2.500 min | 0.0% |
| 40.000 min | 70.0% |
| 45.000 min | 100.0% |
| 52.000 min | 100.0% |
| 54.000 min | 0.0% |
| 60.000 min | End |

Example 5: CRHR2 and CRHR1 Agonist Activity cAMP Assay

Figure 2:
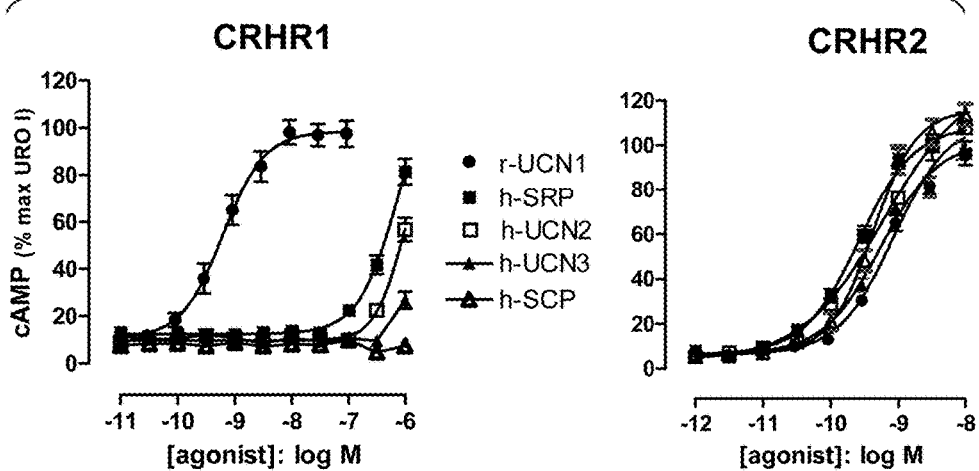
FIG. 2 shows the agonist potency and selectivity of peptide agonists against human CRHR1 and CRHR2, respectively.

The CRHR2 and CRHR1 agonist activity of the CRH family was characterized in two lines of SK-N-MC (human neuroblastoma) cells transfected with either the human CRHR2 or human CRHR1 in an adenosine 3',5'-cyclic monophosphate (cAMP) assay. h-SCP (SEQ ID NO:1) was equipotent with h-UCN2 (SEQ ID NO:115) in this assay and shown to be the most selective CRHR2 agonist in the CRH family (FIG. 2). The concentration required for 50% maximum effect ($A_{50}$) was 0.4 nM.

Human CRHR1 (accession number X72304) or CRHR2 (accession number U34587) were cloned into pcDNA3.1/Zeo expression vector and stably transfected into SK-N-MC cells by electroporation. Cells were maintained in MEM w/Earl's Salt with 10% FBS, 50 I.U. penicillin, 50 μg/ml streptomycin, 2 mM L-glutamine, 1 mM sodium pyruvate and 0.1 mM nonessential amino acids, 600 μg/ml G418. Cells were grown at 37° C. in 5% $CO_2$.

Cells were plated in 96-well tissue culture dishes (Biocoat from BD Biosciences) overnight at 50,000 cell/well. Cells were washed with PBS then resuspended in DMEM F-12 without phenol red, containing 10 μM isobutylmethylxanthine (IBMX). Cells were incubated with the peptides at concentrations ranging from 1 pM to 10 μM for 60 min at 37° Celsius. For subsequent evaluation of any antagonism activity of those peptides that did not produce an agonist response, the peptides were pre-incubated at 10 μM for 20 min prior to the addition of h-SCP for 60 min. Forskolin (10 μM), a direct stimulant of adenylate cyclase, was used as positive control. The assays were stopped by the addition of 0.5 M HCl and mixing by orbital rotation for 2 h at 4° Celsius.

To assess the activity of the inventive peptide at the CRHR2, an intracellular cAMP measurement test using a Flash plate radioactive assay (Catalog No. Cus56088; Perkin Elmer, MA, U.S.A.) was employed.

Transfected SK-N-MC cells were plated in 96-well Biocoat tissue culture dishes (BD Biosciences, San Jose, Calif., U.S.A) overnight at 50,000 cell/well. Cells were first washed with PBS and then suspended with DMEM/F-12 without phenol red, containing μM isobutylmethylxanthine (IBMX). Suspended cells were transferred into a 96-well flash plate coated with scintillant fluid. Cells were incubated with peptides ranging from 1 μM to 1 μM, for 60 min, at 37° Celsius. Forskolin at 10 μM was used as positive control. After ligand stimulation, cells were lysed by the addition of 0.5M HCl and mixed by orbital rotation for 2 h at 4° Celsius in order to release intracellular cAMP into the media.

Media containing released intracellular cAMP was transferred to a 96-well flash plate coated with scintillant fluid containing an anti-cAMP antibody. In this assay, intracellular cAMP competes with $^{125}$I-labeled cAMP binding to the antibody. To generate a standard curve, cAMP ranging from 2.5 to 250 pmoles/ml was included in the experiment. [$^{125}$I]-cAMP was measured on a TopCount scintillation counter (Perkin Elmer, MA, U.S.A).

Individual agonist concentration-response curve data were fitted to the Hill equation, see formula below, using GraphPad Prism (Graphpad Software, La Jolla, Calif., U.S.A.), to provide estimates of agonist concentration needed to generate one-half maximal response ($A_{50}$), and the maximal asymptote ($\alpha$) and Hill slope ($n_H$) parameters. In this equation, [A] is the agonist concentration and E is the measured effect:

$$E = \frac{\alpha \cdot [A]^{n_H}}{[A]_{50}^{n_H} + [A]^{n_H}}$$

For display purposes the mean fitted parameter estimates were used to generate a single E/[A] curve shown superimposed on the mean experimental data. Potency estimates for agonists, $pA_{50}$, are expressed as the negative logarithm of the midpoint of each curve and listed with their standard error of measurement (SEM). Logarithm base 10 of the agonist dose ratio (Log DR) values were calculated by subtraction of the test compound $pA_{50}$ value from the corresponding h-SCP (SEQ ID NO:1) control $pA_{50}$ value within the same assay batch. The SEM values of the Log DR values are given by the square root of the sum of the squared SEM values of the h-SCP (SEQ ID NO:1) control and test compound $pA_{50}$ values.

TABLE 10

CRHR antagonist peptide-anti-sauvagine-30

FHLLR KMIEI EKQEK EKQQA ANNRL SV30 SEQ ID NO: 118
LLDTI-NH$_2$

Figure 3:
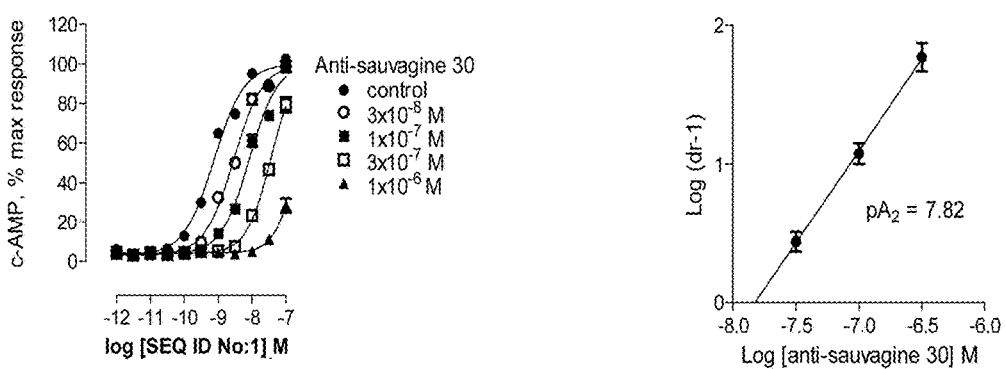
FIG. 3 displays the effects of competitive antagonism between a peptide agonist with SEQ ID NO:1 and anti-sauvagine-30 (SEQ ID NO:118).

The CRHR2-mediated cAMP response to h-SCP (SEQ ID NO:1) was blocked by the selective CRHR2 antagonist, anti-sauvagine-30 (SV30, SEQ ID NO:118 listed in Table 9), in a concentration-dependent manner consistent with surmountable competitive antagonism (FIG. 3). The presence of anti-sauvagine-30 yielded a $pA_2$ value of 7.82 for the compound of SEQ ID NO:1.

TABLE 10

| | | | | | | | | | |
|---|---|---|---|---|---|---|---|---|---|
| TKFTL SLDVP TNIMN LLFNI AKAKN LRAQA AANAH LMAQI | | | | | | | | non-amidated h-SCP | SEQ ID NO: 113 |
| DDPPL SIDLT FHLLR TLLEL ARTQS QRERA EQNRI IFDSV-NH$_2$ | | | | | | | | r-UCN1 | SEQ ID NO: 114 |
| IVLSL DVPIG LLQIL LEQAR APAAR EQATT NARIL ARV-NH$_2$ | | | | | | | | h-UCN2 | SEQ ID NO: 115 |
| HPGSR IVLSL DVPIG LLQIL LEQAR APAAR EQATT NARIL ARV-NH$_2$ | | | | | | | | h-SRP | SEQ ID NO: 117 |

Human and rat peptides (see Table 10) were used on the stimulation of h-CRHR1 or h-CRHR2 transfected SK-N-MC cells in the cAMP flash plate assay. Peptides were incubated for 1 hr at 37° Celsius. Curves were calculated using non-linear regression sigmoidal concentration-response analysis calculation in GraphPad Prism. The so obtained $pA_{50}$ values are shown in Table 11 in addition to literature values.

TABLE 11

| | | Published | Experimental | | | | | | |
|---|---|---|---|---|---|---|---|---|---|
| Receptor | Peptide | $pA_{50}$ | $pA_{50}$ | SEM | $n_H$ | SEM | $\alpha_{max}$ | SEM | n |
| CRHR1 | r-UCN1 | 9.82[1] | *9.19* | *0.07* | *1.15* | *0.19* | *99.61* | *3.28* | *12* |
| CRHR1 | h-SRP | >7[3] | 6.34 | 0.03 | 1.61 | 0.15 | NA | | 20 |
| CRHR1 | h-SRP | >7[3] | 6.2 | 0.04 | 1.33 | 0.17 | NA | | 11 |
| CRHR1 | h-SRP | >7[3] | 6.28 | 0.03 | 1.26 | 0.13 | NA | | 17 |
| CRHR1 | h-UCN2 | | 6.02 | 0.02 | 1.69 | 0.18 | NA | | 15 |
| CRHR1 | h-UCN3 | <5 | | | | | | | |
| CRHR1 | h-SCP | <5 | | | | | | | |
| CRHR2 | r-UCN1 | 10.06[2] | 9.08 | 0.05 | 1.07 | 0.11 | 110.5 | 2.49 | 12 |
| CRHR2 | h-UCN2 | 9.37[2]/9.12[5] | 8.04 | 0.05 | 0.9 | 0.09 | 114.7 | 2.89 | 16 |
| CRHR2 | h-UCN3 | 9.92[2] | 9.26 | 0.05 | 1.02 | 0.11 | 101.8 | 2.18 | 12 |
| CRHR2 | h-SCP | ~9[4] | 9.41 | 0.06 | 0.99 | 0.12 | 99.31 | 2.69 | 16 |
| CRHR2 | h-SRP | ~9[4] | 9.32 | 0.05 | 1.08 | 0.11 | 113.5 | 2.3 | 16 |
| CRHR2 | h-SCP | ~9[4] | 9.15 | 0.03 | 1.04 | 0.06 | 97.53 | 1.29 | 32 |
| CRHR2 | h-SCP | ~9[4] | 9.36 | 0.04 | 1.39 | 0.05 | 116.1 | 2.59 | 20 |
| CRHR2 | h-SCP | ~9[4] | 9.39 | 0.02 | 1.55 | 0.12 | 98.2 | 1.31 | 30 |
| CRHR2 | h-UCN2 | 9.37[2]/9.12[5] | 9.22 | 0.04 | 0.72 | 0.05 | 128.9 | 2.95 | 40 |
| CRHR2 | h-SRP | ~9[4] | 9.58 | 0.05 | 1.06 | 0.13 | 108.7 | 2.48 | 25 |
| CRHR2 | h-SRP | ~9[4] | 9.23 | 0.03 | 0.99 | 0.06 | 98.56 | 1.42 | 36 |

Data in italic represents potency approximations;
NA = data not available due to low potency and limited peptide supply;
values from published data were obtained with the author's in-house synthesized peptides used for cAMP stimulation of the following transfected systems:
[1]h-CRHR1 or
[2]m-CRHR2b transfected CHO-K1 cells (Lewis, K. et al., 2001, PNAS, vol. 98, pp. 7570-5);
[3]h-CRHR1 or
[4]h-CRHR2b transfected HEK-293 cells, approximated values from concentration response curves (Hsu, S. Y. et al., 2001, Nat. Med., vol. 7, pp. 605-11);
[5]m-CRHR2b transfected HEK-293 cells (Brauns, O. et al., 2002, Peptides, vol. 23, pp. 881-888).

The effects of amidation of the C terminal domain of h-SCP on agonist activity, in terms of potency and/or intrinsic activity, were investigated, since recombinant non-amidated peptide libraries would be difficult to assay in the CRHR2 transfected SK-N-MC cells.

To investigate the peptide agonist activity contribution of different amino acids, several modified peptides were synthesized, starting with 1-7 deletions within the N-terminal sequence. Each peptide was dissolved in water at stock concentrations of 1 mM and stored in Eppendorf tubes (Catalog No. 022364111) in aliquots at −40° Celsius. Peptides were thawed out only once, on the day of the experiment, and diluted further in the cAMP assay buffer.

Figure 4:
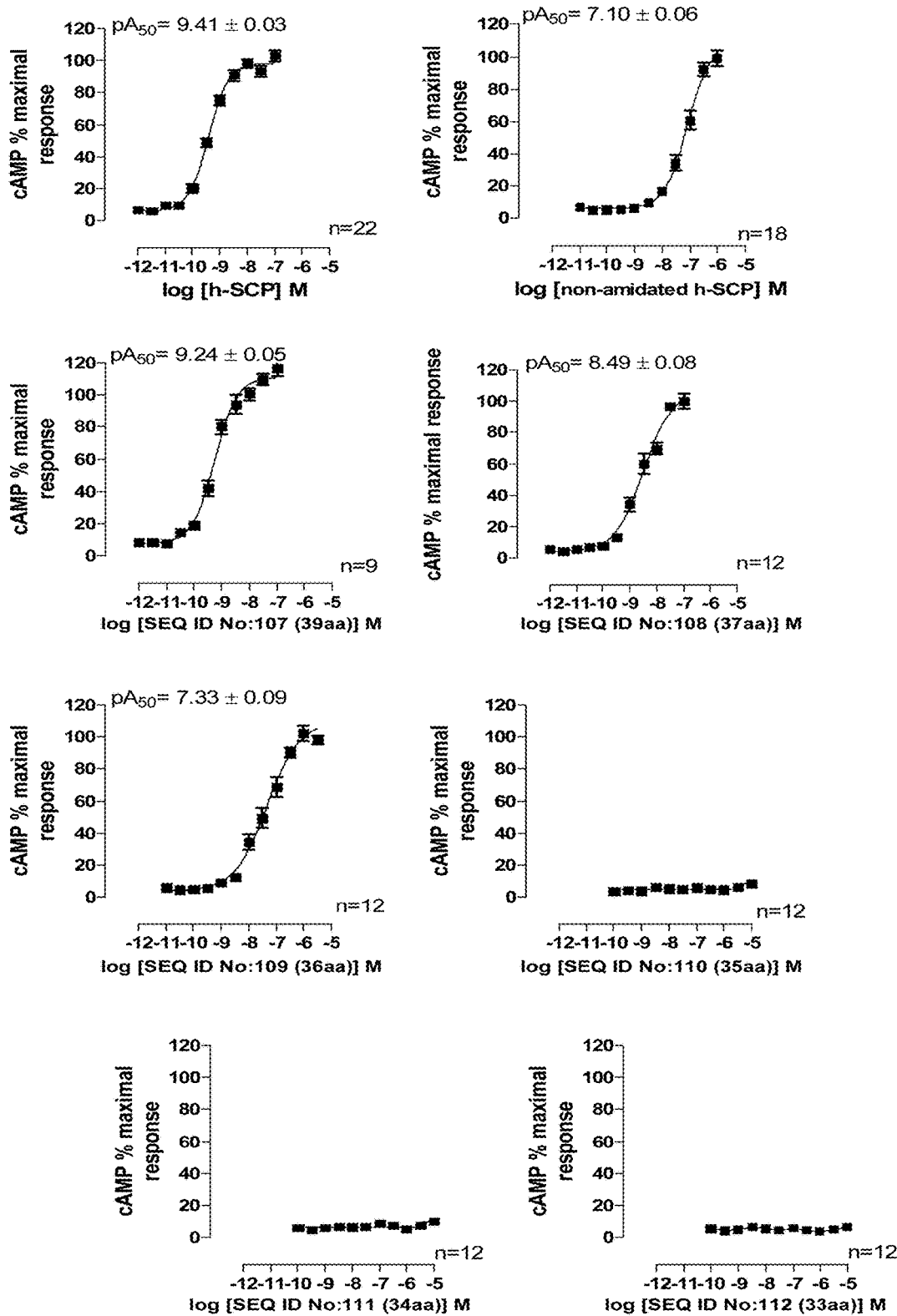
FIG. 4 shows agonist concentration-effect curves of various peptide agonists obtained by measuring cAMP stimulation in h-CRHR2 transfected SK-N-MC cells.

All peptides that produced cAMP in h-CRHR2 transfected SK-N-MC cells, achieved similar maximum responses within each experimental replicate. However the maximal response to h-SCP (SEQ ID NO:1) did vary between daily replicates, so the data were normalized to the maximum response to h-SCP obtained within each replication. Data were then combined from 3-5 replicate experiments for final calculation of the agonist concentration-effect curve parameters (FIG. 4). The $pA_{50}$ values obtained are summarized in Table 12.

Non-amidated h-SCP (SEQ ID NO:113) was approximately 200-fold less potent than the amidated parent peptide although the maximum response was indistinguishable. In one batch the parent 40 amino acid h-SCP peptide (SEQ ID NO:1) produced a $pA_{50}$ value of 9.41±0.03. Terminal amidation while important for potency is not essential and a fully defined concentration-effect curve was obtained with the non-amidated peptide with the same maximum response as the amidated parent peptide.

Figure 5:
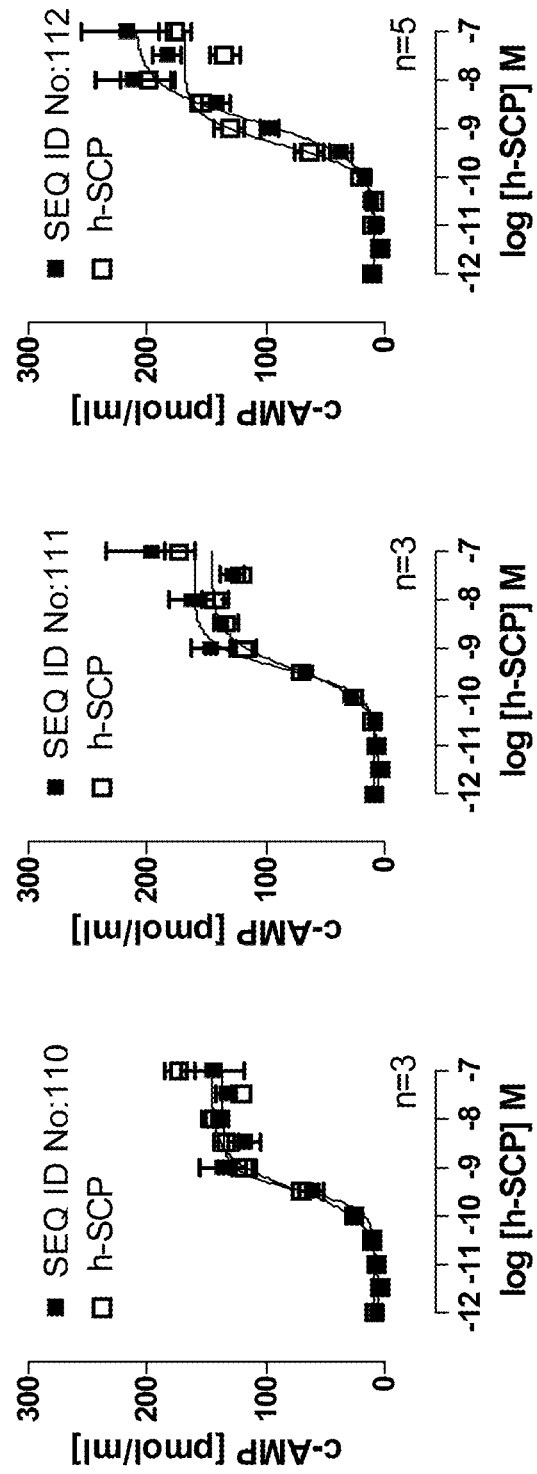
FIG. 5 displays the h-SCP (SEQ ID NO:1) agonist concentration-effect curves measured through cAMP stimulation in h-CRHR2 transfected SK-N-MC cells in the absence and presence of 10 μM of CRHR2 peptide agonists with sequence SEQ ID NO:110, SEQ ID NO:111 and SEQ ID NO:112, respectively.

One amino acid deletion (SEQ ID NO:107) had no significant effect in potency ($pA_{50}$ 9.24±0.05), while the deletion of three (SEQ ID NO:108) and four (SEQ ID NO:109) amino acids resulted in a progressive reduction in $pA_{50}$ values (8.49±0.08 and 7.33±0.9), respectively, and also listed in Table 12. The deletion of five or more amino acids (SEQ ID NO:110, SEQ ID NO:111 and SEQ ID NO:112) resulted in complete loss of agonist activity (FIG. 4). Accordingly, the latter three peptides were tested as antagonists of h-SCP at a concentration of 10 µM (FIG. 5). None of the peptides had a significant effect on the h-SCP concentration-effect curve indicating that the peptides not only had no detectable intrinsic efficacy, but also no significant receptor occupancy, i.e. affinity less than 10 µM.

N-terminal domain deletions of 4 or more amino acids on h-SCP sequence affect the peptide potency. Peptides with one to four amino-acid deletions of the N-terminal domain had progressive reduction in potency, while peptides with deletions of five or more amino-acids resulted in complete loss of agonist activity and receptor affinity ($K_A$>10 µM). The later was expected, based on a previous report of a similar analysis performed on h-UCN2 (Isfort, R. J. et al., 2006, *Peptides*, vol. 27, pp. 1806-1813), since the deletions are close to the conserved amino-acid serine in position 6 and the aspartic acid in position 8.

TABLE 12

| SEQ ID No. | $pA_{50}$ | SEM | $n_H$ | SEM. | $α_{max}$ | SEM | n |
|---|---|---|---|---|---|---|---|
| 1 | 9.41 | 0.04 | 1.18 | 0.11 | 98.68 | 1.59 | 22 |
| 113 | 7.10 | 0.06 | 1.07 | 0.13 | 107.4 | 5.45 | 18 |
| 107 | 9.25 | 0.05 | 1.07 | 0.12 | 111.3 | 2.52 | 9 |
| 108 | 8.49 | 0.08 | 0.82 | 0.10 | 106.3 | 5.05 | 12 |
| 109 | 7.34 | 0.09 | 0.74 | 0.10 | 109.6 | 6.16 | 12 |

TABLE 12-continued

| SEQ ID No. | $pA_{50}$ | SEM | $n_H$ | SEM. | $α_{max}$ | SEM | n |
|---|---|---|---|---|---|---|---|
| 110 | NR | | | | | | 12 |
| 111 | NR | | | | | | 12 |
| 112 | NR | | | | | | 12 |

NR = no response

Furthermore, the effects of cysteine mutation, N-ethylmaleimide capping, and pegylation on the peptide agonist activity was investigated. Control $pA_{50}$ of h-SCP (SEQ ID NO:1) varied for the various assay batches from 9.47 to 9.74 with SEM of 0.03 to 0.11. Again, several modified peptides were synthesized according to the above Schemes, and the assay results for these peptides are listed in Table 13.

TABLE 13

| SEQ ID No. | $pA_{50}$ | SEM | Log DR [M] | SEM | SEQ ID No. | $pA_{50}$ | SEM | Log DR [M] | SEM |
|---|---|---|---|---|---|---|---|---|---|
| 2 | 8.97 | 0.02 | 0.72 | 0.03 | 55 | ~7.93 | | ~1.61 | |
| 3 | 8.97 | 0.03 | 0.72 | 0.03 | 56 | ~7.20 | | ~2.34 | |
| 4 | 8.65 | 0.06 | 1.03 | 0.07 | 57 | ~7.64 | | ~1.90 | |
| 5 | 8.93 | 0.04 | 0.76 | 0.05 | 58 | ~7.14 | | ~2.40 | |
| 6 | 9.07 | 0.04 | 0.61 | 0.05 | 59 | ~7.22 | | ~2.32 | |
| 7 | 7.60 | 0.09 | 2.08 | 0.10 | 60 | ~6.32 | | >3.22 | |
| 8 | ~6.82 | | 2.86 | | 61 | ~6.22 | | >3.32 | |
| 9 | 7.80 | 0.06 | 1.89 | 0.07 | 62 | ~6.06 | | >3.48 | |
| 10 | 8.28 | 0.08 | 1.30 | 0.09 | 63 | ~7.45 | | ~2.12 | |
| 11 | 8.76 | 0.06 | 0.82 | 0.07 | 64 | ~6.98 | | ~2.59 | |
| 12 | 7.86 | 0.10 | 1.72 | 0.11 | 65 | ~6.82 | | ~2.75 | |
| 13 | 9.59 | 0.04 | −0.01 | 0.06 | 66 | 8.31 | 0.04 | 1.26 | 0.05 |
| 14 | ~7.34 | | >2 | | 67 | ~6.35 | | >3 | |
| 15 | 8.68 | 0.04 | 0.90 | 0.06 | 68 | ~6.96 | | ~2.61 | |
| 16 | 8.93 | 0.03 | 0.76 | 0.03 | 69 | 7.45 | 0.05 | 2.09 | 0.05 |
| 17 | 9.50 | 0.07 | 0.02 | 1.02 | 70 | ~7.34 | | ~2.07 | |
| 18 | 8.41 | 0.09 | 1.11 | 1.72 | 71 | ~7.35 | | ~2.26 | |
| 19 | 8.01 | 0.04 | 1.67 | 0.04 | 72 | 8.04 | 0.04 | 1.50 | 0.04 |
| 20 | 9.00 | 0.04 | 0.52 | 0.74 | 73 | 8.29 | 0.10 | 1.11 | 0.18 |
| 21 | 8.75 | 0.06 | 0.77 | 1.44 | 74 | ~7.33 | | ~2.28 | |
| 22 | 9.17 | 0.04 | 0.52 | 0.04 | 75 | 8.24 | 0.06 | 1.30 | 0.06 |
| 23 | 8.55 | 0.03 | 1.13 | 0.04 | 76 | 6.84 | 0.09 | 2.70 | 0.09 |
| 24 | 8.94 | 0.03 | 0.74 | 0.03 | 77 | 8.27 | 0.05 | 1.27 | 0.05 |
| 25 | 9.17 | 0.08 | 0.35 | 2.51 | 78 | ~7.89 | | ~1.52 | |
| 26 | 9.44 | 0.04 | 0.08 | 2.58 | 79 | 8.50 | 0.12 | 1.11 | 0.15 |
| 27 | 8.76 | 0.10 | 0.76 | 2.61 | 80 | 7.60 | 0.10 | 1.75 | 0.15 |
| 28 | 9.36 | 0.07 | 0.16 | 0.09 | 81 | 7.83 | 0.03 | 1.82 | 0.07 |
| 29 | 9.47 | 0.06 | 0.00 | 0.07 | 82 | 8.40 | 0.15 | 1.12 | 0.19 |
| 30 | 8.40 | 0.05 | 1.28 | 0.05 | 83 | 7.91 | 0.05 | 1.63 | 0.05 |
| 31 | 8.02 | 0.08 | 1.61 | 0.09 | 84 | ~6.82 | | ~2.84 | |
| 32 | 9.41 | 0.05 | 0.11 | 2.80 | 85 | 8.51 | 0.08 | 0.89 | 0.17 |
| 33 | 9.07 | 0.06 | 0.45 | 2.83 | 86 | 8.79 | 0.12 | 0.82 | 0.15 |
| 34 | ~6.32 | | >3.19 | | 87 | ~6.00 | | >3.68 | |
| 35 | 8.93 | 0.06 | 0.70 | 0.07 | 88 | 8.12 | 0.03 | 1.55 | 0.04 |
| 36 | 9.10 | 0.07 | 0.42 | 2.88 | 89 | 8.48 | 0.08 | 0.98 | 0.14 |
| 37 | 8.58 | 0.10 | 1.05 | 0.11 | 90 | ~7.49 | | ~2.17 | |
| 38 | ~6.67 | | >2.95 | | 91 | ~6.23 | | >3.43 | |
| 39 | 9.21 | 0.04 | 0.41 | 0.06 | 92 | 8.12 | 0.03 | 1.55 | 0.04 |
| 40 | 9.08 | 0.04 | 0.55 | 0.06 | 93 | 8.20 | 0.04 | 1.47 | 0.04 |
| 41 | 7.45 | 0.27 | 2.07 | 2.94 | 94 | ~7.00 | | >2.39 | |
| 95 | 9.31 | 0.12 | 0.43 | 0.14 | 42 | ~7.75 | | ~1.72 | |
| 96 | 8.74 | 0.11 | 1 | 0.13 | 43 | 9.79 | 0.04 | −0.32 | 0.05 |
| 97 | ~9.00 | | ~0.74 | | 44 | ~7.5 | | ~1.97 | |
| 98 | 9.50 | 0.10 | 0.18 | 0.13 | 45 | 9.48 | 0.05 | −0.01 | 0.06 |
| 99 | 8.94 | 0.1 | 0.8 | 0.12 | 46 | 9.43 | 0.05 | 0.04 | 0.06 |
| 100 | 8.64 | 0.07 | 1.1 | 0.1 | 47 | 9.5 | 0.06 | −0.03 | 0.07 |
| 101 | 7.84 | 0.13 | 1.9 | 0.15 | 48 | 9.44 | 0.05 | 0.03 | 0.06 |
| | | | | | 49 | 9.36 | 0.06 | 0.11 | 0.07 |
| | | | | | 50 | 9.48 | 0.06 | −0.01 | 0.07 |
| | | | | | 51 | 8.79 | 0.04 | 0.68 | 0.05 |
| | | | | | 52 | 9.42 | 0.04 | 0.05 | 0.05 |
| | | | | | 53 | ~7.25 | | ~2.22 | |
| | | | | | 54 | 9.55 | 0.04 | −0.08 | 0.05 |

Results exemplifying the activity profile of various modifications of the inventive peptide are shown in the Table 14 including stresscopin (h-SCP) peptide, urocortin 2 (h-UCN2), and h-SCP-IA-PEG peptide (SEQ ID NO:102), with h-SCP-IA-PEG being a peptide having the SCP sequence with a cysteine substitution in position 28 as set forth in SEQ ID NO:29 and a PEG polymer linked via an acetamide (IA) linker to the cysteine in position 28. The data are the mean±SEM of one to three replicates and are expressed as the % of the maximum response obtained to h-SCP within each replicate experiment.

TABLE 14

| SEQ ID No. | pA$_{50}$ | SEM | n$_H$ | SEM | α$_{max}$ | SEM | n |
|---|---|---|---|---|---|---|---|
| 1 | 9.40 | 0.02 | 1.26 | 0.08 | 100.1 | 1.11 | 28 |
| 115 | 9.51 | 0.02 | 1.34 | 0.09 | 116.9 | 1.33 | 24 |
| 102 | 8.15 | 0.02 | 1.05 | 0.05 | 111.1 | 1.95 | 32 |

The h-SCP-IA-PEG peptide was also incubated in the presence of 100 nM anti-sauvagine-30 a selective competitive antagonist of h-CRHR2 receptor, resulting in a rightward shift in the h-SCP-IA-PEG peptide concentration-response curve with corresponding pA$_{50}$ approximate value of 6.89, when maximal response was constrained to 100%.

Example 6: CRHR1 and CRHR2 Radioligand Binding Activity

The binding profile of h-SCP (SEQ ID NO:1) at CRHR2 was determined in radioligand binding studies in a membrane preparation of SK-N-MC cells stably transfected with human CRHR2 using [$^{125}$I]-anti-sauvagine-30 as the radiolabel. The cells were harvested by cell scraping and resulting pellets immediately frozen at ±80° Celsius (approximately 50×10$^6$ cells/pellet).

Frozen cell pellets were defrosted on ice in 15 ml of assay buffer that was composed of 10 mM HEPES, 130 mM NaCl, 4.7 mM KCl, 5 mM MgCl$_2$, and 0.089 mM bacitracin at pH 7.2 and 21±3° Celsius. The solution was then homogenized with a Polytron tissue grinder at a setting of 10 and 7×3 s (Brinkmann Instruments, Westbury, N.Y.). The homogenate was centrifuged at 4° Celsius at 800×g for 5 min with the pellet being discarded. The supernatant was re-centrifuged at 26,892×g for 25 min at 4° Celsius with the final pellet being re-suspended in assay buffer. All binding assays were conducted in 96-well Multiscreen GF/B filter plates (Millipore, Billericay, Mass., U.S.A.) that were pre-soaked in assay buffer with 0.3% PEI for 1 hour. For competition studies, cell membranes of 45 µl volume were incubated with either 60 µM [$^{125}$I]-anti-sauvagine-30 in 50 µl volume for the CRHR2 assay or with)[$^{125}$I]-(Tyr$^0$)-sauvagine for the CRHR1 assay in the presence of 15 µl of competing ligand for 120 min having a total volume of 150 Nonspecific binding was determined by inclusion of 1 µM of r-UCN1 (SEQ ID NO:114). The bound radioactivity was separated by filtration using a Multiscreen Resist manifold (Millipore Corp., Billerica, Mass., U.S.A). The filters were washed three times with ice-cold PBS at pH 7.5 and radioactivity retained on the filters was quantified by its liquid scintillation measured by a TopCount counter (Packard BioScience, Boston, Mass., U.S.A). All experiments were performed in triplicate.

Data from individual competition curves were expressed as the percentage of specific [$^{125}$I]-anti-sauvagine-30 or) [$^{125}$I]-(Tyr$^0$)-sauvagine binding (B) within each experiment. These data were then analyzed using a four-parameter logistic using GraphPad Prism with the upper (α$_{max}$) and lower (α$_{min}$) asymptotes weighted to 100% and 0%, respectively, by including these values two log units above and below the lowest and highest concentrations of the competitor, respectively:

$$B = \frac{\alpha_{min} + (\alpha_{max} - \alpha_{min})}{1 + 10^{((\log IC_{50} - [L]) \cdot n_H)}}$$

The competition curve obtained with h-SCP (SEQ ID NO:1) was biphasic. This indicated a high and low affinity receptor binding state characterized by a high negative logarithm of the concentration at 50% inhibition (pIC$_{50}$) and a low pIC$_{50}$ of 6.6. The high-affinity site binding was shown to be inhibited by 100 µM guanosine 5'-O-[gamma-thio] triphosphate (GTPγS). In contrast, h-UCN2 (SEQ ID No. 115) exhibited only high affinity binding suggesting that h-UCN2 behaved as an agonist with higher intrinsic efficacy than h-SCP (SEQ ID NO:1) in the assay. pK$_I$ values resulting from this data analysis are shown in Table 15.

TABLE 15

| | Receptor | | | |
| | CRHR1 | | CRHR2 | |
| SEQ Id No. | pK$_I$ | n$_H$ | pK$_I$ | n$_H$ |
|---|---|---|---|---|
| 1 | 4.6 ± 0.28 | 1.16 ± 0.65 | 5.71 ± 0.04 | 1.00 ± 0.04 |
| 114 | 8.69 ± 0.15 | 0.91 ± 0.27 | 8.51 ± 0.05 | 1.19 ± 0.14 |
| 115 | ND | | 7.74 ± 0.05 | 1.28 ± 0.15 |
| 116 | 4.96 ± 1.69 | 0.79 ± 1.21 | 6.49 ± 0.07 | 0.68 ± 0.08 |
| 117 | ND | | 7.57 ± 0.04 | 1.26 ± 0.14 |
| 118 | 5.81 ± 0.20 | 1.00 ± 0.49 | 7.78 ± 0.05 | 1.15 ± 0.12 |

ND = Not detectable

Example 7: Vascular Smooth Muscle Relaxation—Rat Aortic Rings

The ability of h-SCP (SEQ ID NO:1) to relax vascular smooth muscle was examined in isolated, rat aortic rings pre-contracted with phenylephrine (PE) (see FIG. 6). This peptide (SEQ ID NO:1) produced concentration-dependent relaxation with a pA$_{50}$ of 6.05±0.12, but was 10-fold less potent than h-UCN2 (SEQ ID NO:115) having a pA$_{50}$ of 7.01±0.13. The responses caused by h-SCP (SEQ ID NO:1) were inhibited by anti-sauvagine-30 (SEQ ID NO:118).

Example 8: Cardiovascular Characterization in Isolated Rabbit Heart

The effect of h-SCP (SEQ ID NO:1) on heart rate (HR), left ventricular (LV) contraction, and vascular tone was assessed in a retrograde-perfused Langendorff rabbit heart assay. A bolus of a placebo-like control vehicle or h-SCP (SEQ ID NO:1) was administered directly into the perfusion block. h-SCP (SEQ ID NO:1) produced concentration-dependent increases in heart rate and left ventricular developed pressure (dP/dt$_{max}$) and a corresponding decrease in coronary perfusion pressure (CPP) at a concentration for 50% response equal to 52 nM, 9.9 nM, and 46 nM, respectively (FIG. 7), while no response was observed in case of the control vehicle.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A conjugate comprising TKFTLSLDVPTNIMNLLF-NIAKAKNLRCQAAANAHLMAQI (SEQ ID NO: 29) and a linker attached to the cysteine of SEQ ID NO: 29.

2. The conjugate of claim 1, wherein said linker is acetamide of N-ethylsuccinimide.

3. The conjugate of claim 1 further comprising polyethylene glycol (PEG) attached to said linker, wherein said PEG has a molecular weight of not more that about 80 kDa.

4. The conjugate of claim 3, wherein said linker is acetamide.

5. The conjugate of claim 3, wherein said PEG has a molecular weight that is selected from the group consisting of about 2 kDa, about 5 kDa, about 12 kDa, about 20 kDa, about 30 kDa, and about 40 kDa.

6. The conjugate of claim 3, wherein said PEG is branched or linear.

7. The conjugate of claim 3, wherein said PEG further comprises a reactive group.

8. A conjugate having formula:

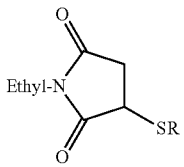

wherein R is TKFTLSLDVPTNIMNLLFNIAKAKNLRC-QAAANAHLMAQI (SEQ ID NO: 29), and the S of said formula is a sulfur atom of a cysteine thiol group of SEQ ID NO: 29.

9. A conjugate of claim 1 having formula

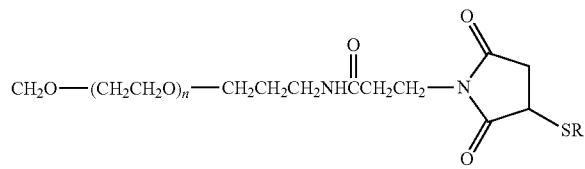

wherein n is an integer in a range from about 40 to about 1900, R is SEQ ID NO: 29 and S is a sulfur atom of a cysteine thiol group of SEQ ID NO: 29.

10. A conjugate of claim 1 having the formula of:

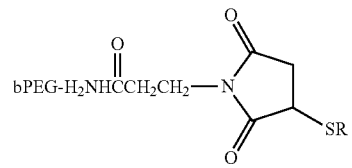

wherein bPEG is a branched polyethylene glycol with a molecular weight of about 80 kDa, R is SEQ ID NO: 29 and S is a sulfur atom of a cysteine thiol group of SEQ ID NO: 29.

11. A conjugate of claim 1 having formula

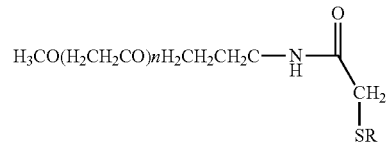

wherein n is an integer in a range from about 40 to about 1900, R is SEQ ID NO: 29 and S is a sulfur atom of a cysteine thiol group of SEQ ID NO: 29.

12. The conjugate of claim 9, wherein n is an integer of about 460.

13. The conjugate of claim 11, wherein n is an integer of about 460.

14. A pharmaceutical composition comprising (a) the conjugate of claim 12; and (b) a pharmaceutically acceptable excipient.

15. A pharmaceutical composition comprising (a) the conjugate of claim 13; and (b) a pharmaceutically acceptable excipient.

16. A method of treating a subject suffering from or diagnosed with a disease, disorder, or medical condition mediated by corticotrophin releasing hormone receptor 2 activity selected from the group consisting of metabolic disease and heart failure, the method comprising administering to a subject in need of such treatment a therapeutically effective amount of a conjugate of claim 1.

17. A method according to claim 16, wherein the disease, disorder, or medical condition is diabetes.

18. A method according to claim 16, wherein the disease, disorder, or medical condition is heart failure.

19. A pharmaceutical composition comprising SEQ ID NO: 29 and a pharmaceutically acceptable excipient.

20. A pharmaceutical composition comprising the conjugate of claim 9 and a pharmaceutically acceptable excipient.

21. A pharmaceutical composition comprising the conjugate of claim 11 and a pharmaceutically acceptable excipient.

* * * * *